United States Patent [19]

Kunisch et al.

[11] Patent Number: 5,108,483

[45] Date of Patent: Apr. 28, 1992

[54] HERBICIDAL 6-HETEROCYCLIC GROUP SUBSTITUTED BENZOXAZINES

[75] Inventors: Franz Kunisch, Odenthal-Gloebusch; Klaus Lürssen, Bergisch Gladbach; Hans-Joachim Santel, Leverkusen; Robert R. Schmidt, Bergisch Gladbach, all of Fed. Rep. of Germany

[73] Assignee: Bayer Aktiengesellschaft, Leverkusen, Fed. Rep. of Germany

[21] Appl. No.: 590,418

[22] Filed: Sep. 28, 1990

[30] Foreign Application Priority Data

Nov. 4, 1989 [DE] Fed. Rep. of Germany ....... 3936826

[51] Int. Cl.$^5$ ..................... A01N 43/00; A01N 43/48; A01N 43/64; C07D 265/36
[52] U.S. Cl. .......................................... 71/88; 71/92; 71/94; 71/95; 544/73; 544/105
[58] Field of Search .................... 544/93, 94, 96, 105, 544/73, 105; 71/92, 88, 94, 95

[56] References Cited

U.S. PATENT DOCUMENTS

| | | | |
|---|---|---|---|
| 3,865,818 | 2/1975 | Krapcho et al. | 544/73 |
| 4,729,784 | 3/1988 | Kume et al. | 71/95 |
| 4,792,605 | 12/1988 | Nagano et al. | 544/105 |
| 4,798,620 | 1/1989 | Kume et al. | 71/95 |
| 4,877,444 | 10/1989 | Enomoto et al. | 71/92 |
| 4,902,335 | 2/1990 | Kume et al. | 71/90 |

FOREIGN PATENT DOCUMENTS

| | | |
|---|---|---|
| 0263299 | 4/1988 | European Pat. Off. |
| 1-140570 | 6/1986 | Japan. |
| 277383 | 12/1987 | Japan. |

OTHER PUBLICATIONS

192429F: H. Toru et al., "Preparation of 5-fluoro-2-nitrophenol as intermediate for herbicides"; Chem. Abstr., V. 110, 1989, pp. 708.

Primary Examiner—Mukund J. Shah
Assistant Examiner—Matthew U. Grumbling
Attorney, Agent, or Firm—Sprung Horn Kramer & Woods

[57] ABSTRACT

Herbicidal nitrogen-containing N-aryl-heterocycles of the formula

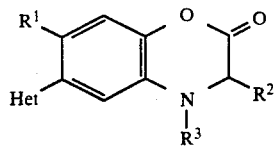

in which
Het represents a heterocycle of the formula

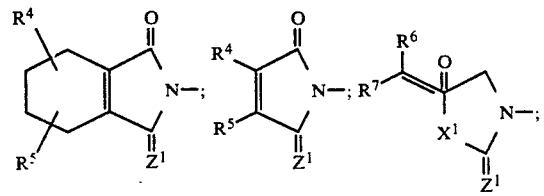

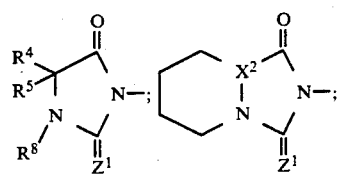

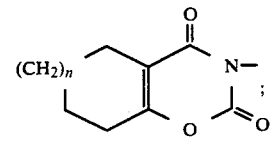

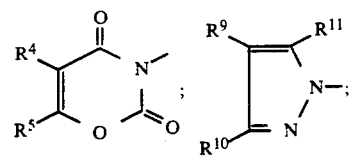

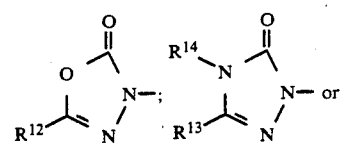

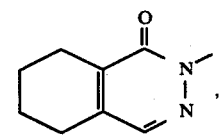

$X^1$ represents oxygen, a —CH$_2$— group or an

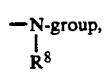

$X^2$ represents nitrogen or a CH group,
$Z^1$ represents oxygen or sulphur and
n represents the number 0 or 1.

11 Claims, No Drawings

HERBICIDAL 6-HETEROCYCLIC GROUP SUBSTITUTED BENZOXAZINES

The invention relates to new nitrogen-containing N-aryl-heterocycles, to several processes and to new intermediates for their preparation, and to their use as herbicides.

It is already known that certain nitrogen-containing N-aryl-heterocycles have herbicidal properties (cf. for example, EP-A 61,741, EP-A 83,055 or EP-A 200,872).

New nitrogen-containing N-aryl-heterocycles of the general formula (I)

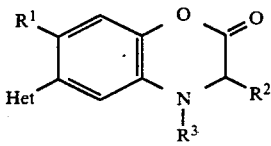

in which
Het represents a heterocycle of the formula

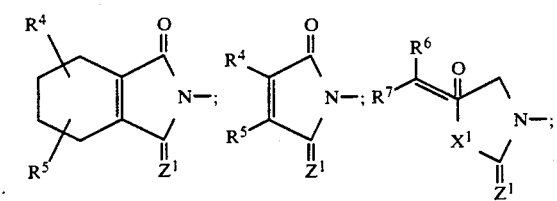

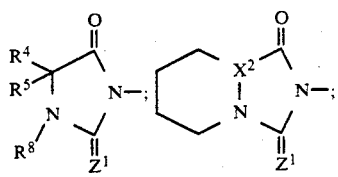

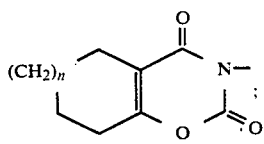

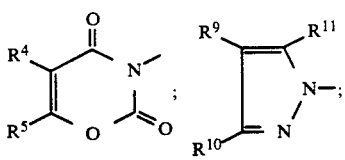

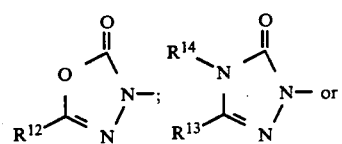

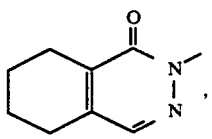

$R^1$ represents hydrogen or halogen,
$R^2$ represents hydrogen or alkyl,
$R^3$ represents hydrogen or in each case optionally substituted alkyl, alkenyl, alkynyl, cycloalkyl, cycloalkenyl, alkylsuphonyl, arylsulphonyl, alkylcarbonyl or alkoxycarbonyl, $R^4$ and $R^5$ independently of one another in each case represent hydrogen or alkyl, $R^6$ and $R^7$ independently of one another in each case represent hydrogen or alkyl or together represent a divalent alkanediyl radical, $R^8$ represents hydrogen, alkyl or optionally substituted aryl, $R^9$ represents hydrogen, halogen, alkyl or halogenoalkyl, $R^{10}$ represents hydrogen, alkyl or halogenoalkyl or $R^9$ and $R^{10}$ together represent divalent alkanediyl, $R^{11}$ represents hydrogen, halogen, alkyl or halogenoalkyl, $R^{12}$ and $R^{13}$ independently of one another represent hydrogen, alkyl, alkoxyalkyl, halogenoalkyl, alkenyl, halogenoalkenyl, alkynyl or halogenoalkynyl, or represent optionally substituted cycloalkyl, $R^{14}$ represents hydrogen, alkyl, halogenoalkyl, alkenyl, halogenoalkenyl, alkynyl or halogenoalkynyl or $R^{13}$ and $R^{14}$ together represent divalent alkanediyl, $X^1$ represents oxygen, a —CH$_2$— group or an

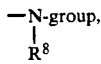

$X^2$ represents nitrogen or a CH group,
$Z^1$ represents oxygen or sulphur and
n represents the number 0 or 1, have been found.

The radicals ($R^1$, $R^2$, Het, etc.) which are defined in the active compounds of the formula (I) likewise have the meanings given in the compounds of the formula (I) for all defined ranges when they occur in the intermediates and precursors. This also applies correspondingly to those radicals which are mentioned several times in precursors and intermediates.

Furthermore, it has been found that the new nitrogen-containing N-aryl-heterocycles of the formula (I) are obtained by one of the processes described below:

(a) nitrogen-containing N-aryl-heterocycles of the formula (Ia)

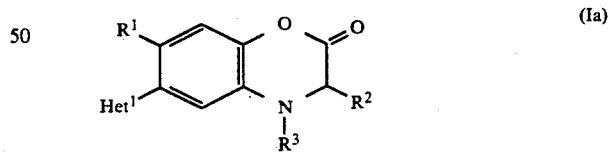

in which
Het$^1$ represents a hetercycle of the formula

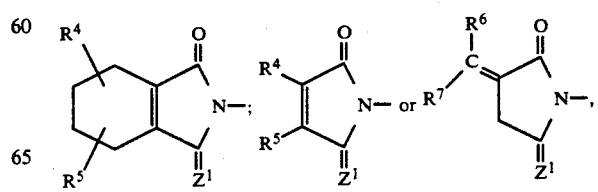

are obtained when anhydrides of the formula (II)

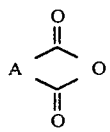

in which
A represents a radical of the formula

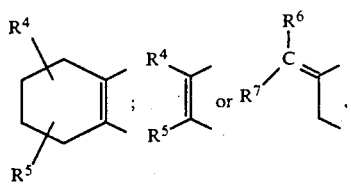

are reacted with aminobenzoxazinones of the formula (III)

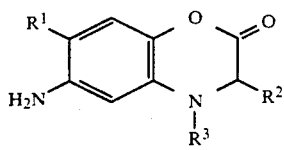

(III)

if appropriate in the presence of a diluent and if appropriate in the presence of a reaction auxiliary;

(b) nitrogen-containing N-aryl-heterocycles of the formula (Ib)

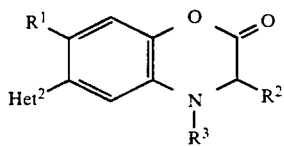

(Ib)

in which
$Het^2$ represents a heterocycle of the formula

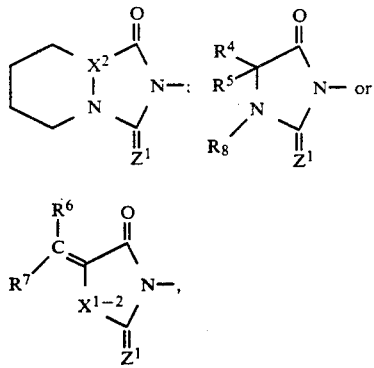

where
$X^{1-2}$ represents oxygen or an

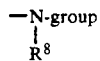

are obtained when carboxylic esters of the formula (IV)

$$R^{15}-COOR^{16} \quad (IV)$$

in which
$R^{15}$ represents a radical of the formula

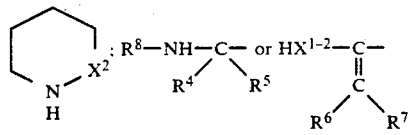

and
$R^{16}$ represents alkyl,
or acid addition salts thereof,
are reacted with iso(thio)cyanates of the formula (V)

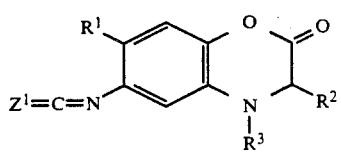

(V)

if appropriate in the presence of a diluent and if appropriate in the presence of a reaction auxiliary;

(c) nitrogen-containing N-aryl-heterocycles of the formula (Ic)

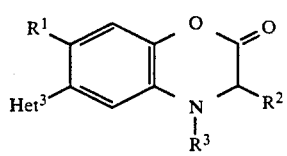

(Ic)

in which
$Het^3$ represents a heterocycle of the formula

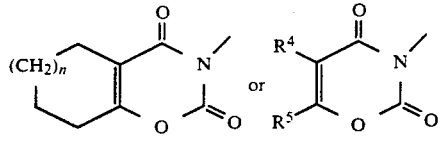

are obtained when compounds of the formulae (VIa) or (VIb)

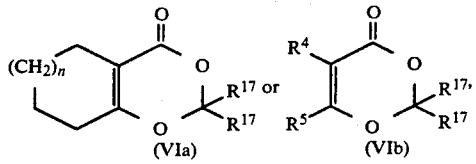

in which
$R^{17}$ represents alkyl, preferably $C_{1-4}$-alkyl, in particular methyl or ethyl,
are reacted with isocyanates of the formula (Va)

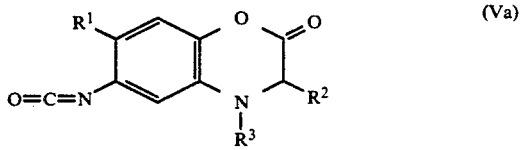

(Va)

in which
$R^3$ has the meaning given above with the exception of hydrogen,
if appropriate in the presence of a diluent and if appropriate in the presence of a reaction auxiliary;

(d) nitrogen-containing N-aryl-heterocycles of the formula (Id)

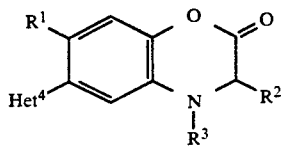

(Id)

in which
Het⁴ represents a heterocycle of the formula

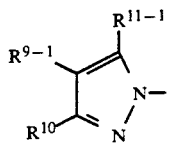

where
$R^{9-1}$ represents hydrogen, alkyl or halogenoalkyl, or together with $R^{10}$ represents a divalent alkanediyl radical, and
$R^{11-1}$ represents hydrogen, alkyl or halogenoalkyl and
$R^{10}$ has the abovementioned meaning,
are obtained when phenylhydrazines of the formula (VII)

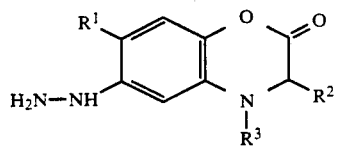

(VII)

are reacted with 1,3-diketones of the formula (VIII)

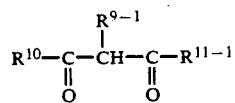

or with derivatives of these diketones, such as, for example, enol ethers, enol esters, ketals, enol ether ketals, enamines or β-halogenovinyl ketones, if appropriate in the presence of a diluent and if appropriate in the presence of a reaction auxiliary;

(e) nitrogen-containing N-aryl-heterocycles of the formula (Ie)

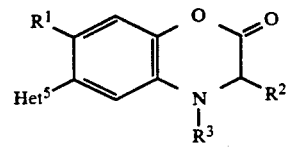

(Ie)

in which
Het⁵ represents a heterocycle of the formula

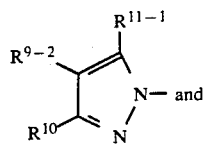

$R^{9-2}$ represents halogen,
are obtained when nitrogen-containing N-aryl-heterocycles of the formula (If)

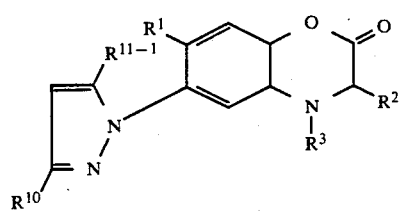

(If)

are reacted with a halogenating agent, if appropriate in the presence of a diluent;

(f) nitrogen-containing N-aryl-heterocylces of the formula (Ig)

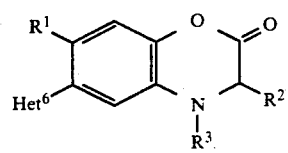

(Ig)

in which
Het⁶ represents a heterocycle of the formula

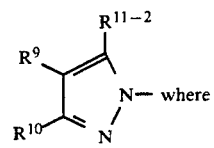

where $R^{11-2}$ represents halogen,
are obtained when N-aryl-pyrazolinones of the formula (IX)

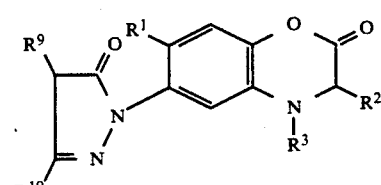

(IX)

are reacted with a halogenating agent, if appropriate in the presence of a diluent and if appropriate in the presence of a reaction auxiliary;

(g) nitrogen-containing N-aryl-heterocycles of the formula (Ih)

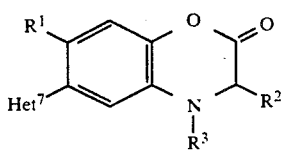

in which
Het⁷ represents a heterocycle of the formula

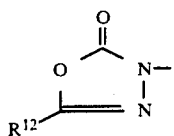

are obtained when phenyl hydrazides of the formula (X)

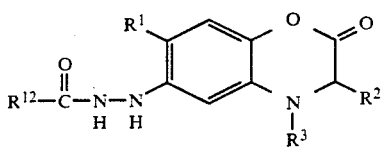

(X)

are reacted with phosgene, if appropriate in the presence of a diluent and if appropriate in the presence of a reaction auxiliary;

(h) nitrogen-containing N-aryl-hetercycles of the formula (Ii)

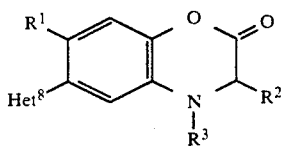

(Ii)

in which
Het⁸ represents a hetercycle of the formula

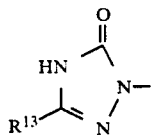

are obtained when phenylhydrazines of the formula (VII)

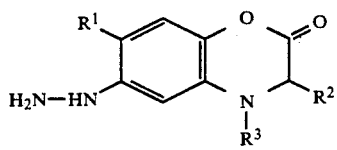

(VII)

are reacted with iminocarboxylic esters of the formula (XI)

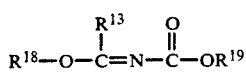

(XI)

in which $R^{18}$ and $R^{19}$ independently of one another in each case represent alkyl, if appropriate in the presence of a diluent;

(i) nitrogen-containing N-aryl-heterocycles of the formula (Ij)

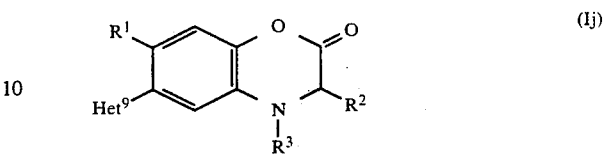

(Ij)

in which
Het⁹ represents a heterocycle of the formula

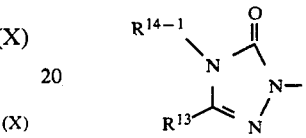

in which
$R^{14-1}$ represents alkyl, halogenoalkyl, alkenyl, halogenoalkenyl, alkynyl or halogenoalkynyl,
are obtained when nitrogen-containing N-aryl-heterocycles of the formula (Ii)

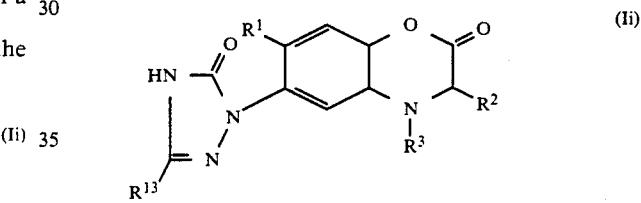

(Ii)

are reacted with alkylating agents of the formula (XII)

$R^{14-1}$—$E^1$ (XII)

in which
$R^{14-1}$ has the abovementioned meaning and
$E^1$ represents an electron-attracting leaving group,
if appropriate in the presence of a diluent and if appropriate in the presence of a reaction auxiliary;

(j) nitrogen-containing N-aryl-heterocycles of the formula (Ik)

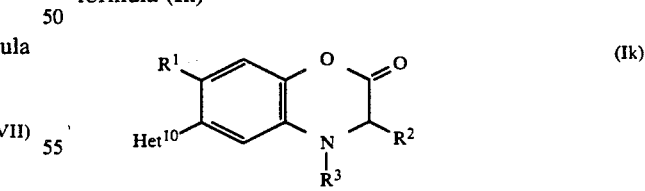

(Ik)

in which
Het¹⁰ represents a heterocycle of the formula

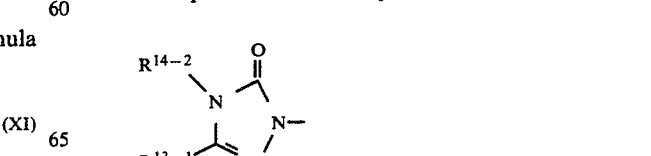

where $R^{13-1}$ and $R^{14-2}$ together represent a divalent alkanediyl radical,
are obtained when amidrazones of the formula (XIII)

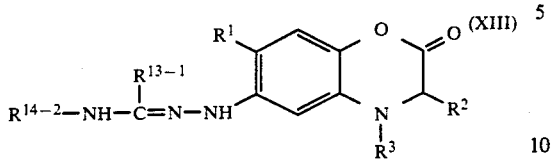
(XIII)

are reacted with phosgene, if appropriate in the presence of a diluent and if, appropriate in the presence of a reaction auxiliary;

(k) nitrogen-containing N-aryl-heterocycles of the formula (Il)

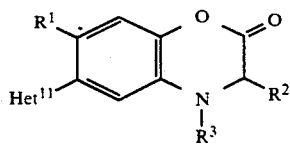
(Il)

in which
Het$^{11}$ represents a heterocycle of the formula

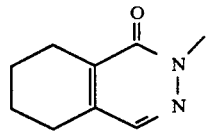

are obtained when hydroxyisobenzofuranone, of the formula (XIV),

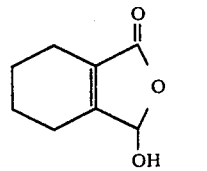
(XIV)

is reacted with phenylhydrazines of the formula (VII)

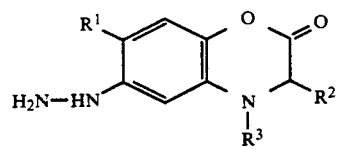
(VII)

if appropriate in the presence of a diluent and if appropriate in the presence of a reaction auxiliary;

(l) nitrogen-containing N-aryl-heterocycles of the formula (Im)

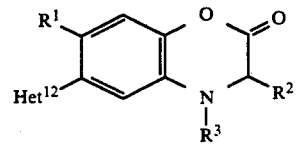
(Im)

in which
Het$^{12}$ represents a heterocycle of the formula

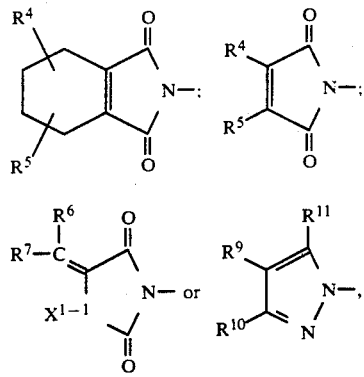

are obtained when nitrogen-containing N-aryl-heterocycles of the formula (In)

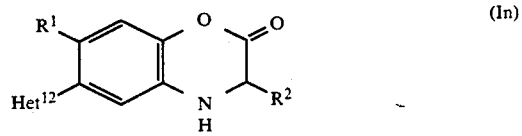
(In)

are reacted with alkylating or acylating agents of the formula (XVI)

$$R^3\text{—}E^2 \qquad (XVI)$$

in which
$R^3$ has the abovementioned meaning with the exception of hydrogen and
$E^2$ represents an electron-attracting leaving group,
if appropriate in the presence of a diluent and if appropriate in the presence of a reaction auxiliary.

Finally, it has been found that the new nitrogen-containing N-aryl-heterocycles of the formula (I) have an excellent selectivity towards useful plants and excellent herbicidal properties.

The saturated or unsaturated hydrocarbon chains in the definitions, such as, for example, alkyl, alkoxy, alkylsulphonyl, alkenyl, alkynyl, or cycloalkylalkyl, are in each case straight-chain or branched.

Halogen generally represents fluorine, chlorine, bromine or iodine. Halogen preferably represents fluorine, chlorine or bromine, in particular fluorine or chlorine.

Preferred nitrogen-containing N-aryl-heterocycles of the formula (I) are those in which Het represents a heterocycle of the formula

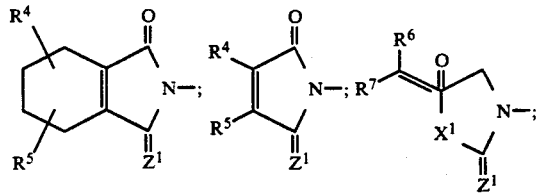

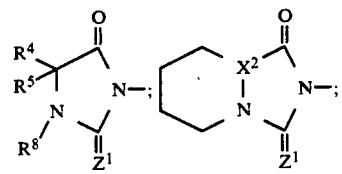

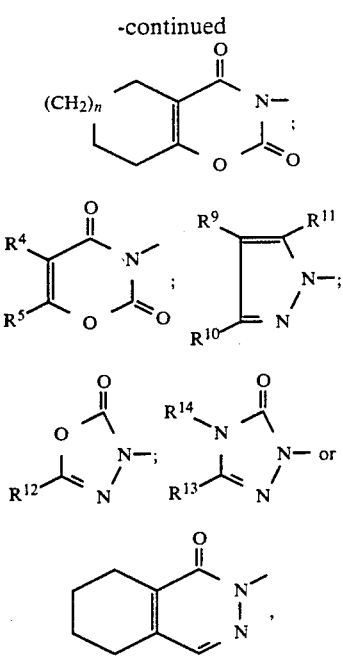

R¹ represents hydrogen or halogen,

R² represents hydrogen or alkyl having 1 to 4 carbon atoms,

R³ represents hydrogen, alkyl having 1 to 8 carbon atoms, alkenyl having 2 to 8 carbon atoms, alkynyl having 3 to 8 carbon atoms, halogenoalkyl having 1 to 8 carbon atoms and 1 to 17 identical or different halogen atoms, halogenoalkenyl having 2 to 8 carbon atoms and 1 to 15 identical or different halogen atoms, halogenoalkynyl having 3 to 8 carbon atoms and 1 to 13 identical or different halogen atoms, alkylsulphonyl, cyanoalkyl, alkoxyalkyl, alkylthioalkyl, halogenoalkoxyalkyl, alkoxyalkoxyalkyl, bis-(alkoxy)alkyl, bis-(alkylthio)alkyl, alkylcarbonyl, alkoxycarbonyl, alkylcarbonylalkyl, alkoxycarbonylalkyl or alkoxyalkoxycarbonylalkyl, each of which has 1 to 8 carbon atoms in the individual alkyl moieties and where appropriate 1 to 9 identical or different halogen atoms, or represents cycloalkyl, cycloalkenyl, cycloalkyloxycarbonylalkyl or cycloalkylalkyl, each of which has 3 to 7 carbon atoms in the cycloalkyl moiety and where appropriate 1 to 4 carbon atoms in the alkyl moiety and each of which is optionally monosubstituted or polysubstituted by identical or different substituents, suitable substituents in the cycloalkyl moiety in each case being: halogen, and also alkyl or alkoxy, in each case having 1 to 4 carbon atoms, and R³ furthermore represents oxetanylalkyl, tetrahydrofuranylalkyl or tetrahydropyranylalkyl, each of which has 1 to 3 carbon atoms in the specific alkyl moieties and each of which is optionally substituted by alkyl having 1 to 4 carbon atoms, and also represents aralkyl which has 6 to 10 carbon atoms in the aryl moiety and 1 to 4 carbon atoms in the alkyl moiety or arylsulphonyl which has 6 to 10 carbon atoms, each of these aralkyl or arylsulphonyl substituents being optionally monosubstituted or polysubstituted by identical or different substituents, suitable aryl substituents in each case being: halogen, cyano, nitro, or alkyl, alkoxy, alkylthio or alkoxycarbonyl, each of which has 1 to 4 carbon atoms, or halogenoalkyl, halogenoalkoxy or halogenoalkylthio, each of which has 1 to 4 carbon atoms and 1 to 9 identical or different halogen atoms, R⁴ and R⁵ independently of one another in each case represent hydrogen or alkyl having 1 to 4 carbon atoms, R⁶ and R⁷ independently of one another in each case represent hydrogen or alkyl having 1 to 4 carbon atoms, or together represent a divalent alkanediyl radical having 2 to 7 carbon atoms, R⁸ represents hydrogen, or alkyl having 1 to 4 carbon atoms, or represents phenyl which is optionally monosubstituted or polysubstituted by identical or different substituents, suitable substituents being: halogen, cyano, nitro or alkyl, alkoxy or alkylthio, each of which has 1 to 4 carbon atoms, and halogenoalkyl, halogenoalkoxy or halogenoalkylthio, each of which has 1 to 4 carbon atoms and 1 to 9 identical or different halogen atoms, and R⁹ represents hydrogen, fluorine, chlorine, bromine, iodine, alkyl having 1 to 6 carbon atoms, or halogenoalkyl having 1 to 4 carbon atoms and 1 to 9 identical or different halogen atoms, or R¹⁰ represents hydrogen, alkyl having 1 to 6 carbon atoms, or halogenoalkyl having 1 to 4 carbon atoms and 1 to 9 identical or different halogen atoms, or R⁹ and R¹⁰ together represent a divalent alkanediyl radical having 2 to 6 carbon atoms, R¹¹ represents hydrogen, fluorine, chlorine, bromine, iodine, alkyl having 1 to 6 carbon atoms, or halogenoalkyl having 1 to 4 carbon atoms and 1 to 9 identical or different halogen atoms, R¹² represents hydrogen, alkyl having 1 to 6 carbon atoms, alkenyl having 3 to 6 carbon atoms, alkynyl having 3 to 6 carbon atoms, halogenoalkyl having 1 to 4 carbon atoms and 1 to 9 identical or different halogen atoms, halogenoalkenyl having 3 to 6 carbon atoms and 1 to 5 identical or different halogen atoms, halogenoalkynyl having 3 to 6 carbon atoms and 1 to 5 identical or different halogen atoms, or alkoxyalkyl having 1 to 4 carbon atoms in each of the individual alkyl moieties, or represents cycloalkyl which has 3 to 7 carbon atoms and which is optionally monosubstituted or polysubstituted by identical or different substituents, suitable substituents being halogen, or alkyl or alkoxy each of which has 1 to 4 carbon atoms, R¹³ represents hydrogen, alkyl having 1 to 6 carbon atoms, alkenyl having 3 to 6 carbon atoms, alkinyl having 3 to 6 carbon atoms, halogenoalkyl having 1 to 4 carbon atoms and 1 to 9 identical or different halogen atoms, halogenoalkenyl having 3 to 6 carbon atoms and 1 to 5 identical or different halogen atoms, halogenoalkinyl having 3 to 6 carbon atoms and 1 to 5 identical or different halogen atoms, or alkoxyalkyl having 1 to 4 carbon atoms in each of the individual alkyl moieties, or represents cycloalkyl which has 3 to 7 carbon atoms and which is optionally monosubstituted or polysubstituted by identical or different substituents, suitable substituents being halogen or alkyl or alkoxy each of which has 1 to 4 carbon atoms, and R¹⁴ represents hydrogen, alkyl having 1 to 6 carbon atoms, alkenyl having 3 to 6 carbon atoms, alkynyl having 3 to 6 carbon atoms, halogenoalkyl having 1 to 4 carbon atoms and 1 to 9 identical or different halogen atoms, halogenoalkenyl having 3 to 6 carbon atoms and 1 to 5 identical or different halogen atoms, or halogenoalkynyl having 3 to 6 carbon atoms and 1 to 5 identical or different halogen atoms, or R¹³ and R¹⁴ together represent a divalent alkanediyl radical having 2 to 6 carbon atoms, X¹ represents oxygen, a CH₂ group or a —N-group,
|
R⁸

X² represents nitrogen or a CH group,
Z¹ represents oxygen or sulphur and
n represents the number 0 or 1.

Particularly preferred nitrogen-containing N-aryl-heterocycles of the formula (I) are those in which Het represents a heterocycle of the formula

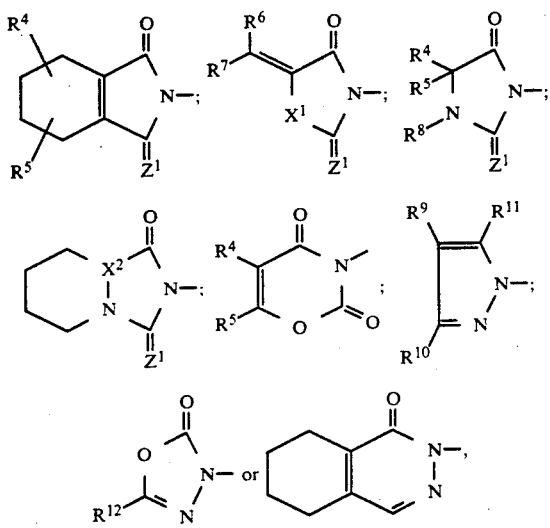

in particular a heterocycle of the formula

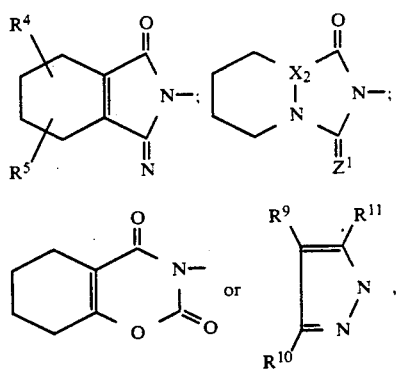

R₁ represents hydrogen, fluorine, chlorine, or bromine,

R₂ represents hydrogen, methyl or ethyl,

R₃ represents methyl, ethyl, n- or i-propyl, n-, i-, s-, or t-butyl, or represents allyl or propargyl, or represents in each case straight-chain or branched pentyl, hexyl, butenyl, pentenyl, hexenyl, butynyl, pentynyl, or hexynyl, and furthermore represents halogenoalkyl having 1 to 4 carbon atoms or halogenoalkenyl having 3 to 5 carbon atoms and in each case 1 to 8 identical or different halogen atoms, in particular fluorine, chlorine or bromine, or represents cyanoalkyl, alkoxyalkyl, alkylthioalkyl, alkylsulphonyl, halogenoalkoxyalkyl, alkoxyalkoxyalkyl, alkylcarbonyl, alkoxycarbonyl, alkylcarbonylalkyl, alkoxycarbonylalkyl or alkoxyalkoxycarbonylalkyl, each of which has 1 to 5 carbon atoms in the individual alkyl moieties, furthermore represents cyclopropylmethyl, cyclopentylmethyl, cyclohexylmethyl, cyclopropyloxycarbonylmethyl, cyclopentyloxycarbonylmethyl, cyclohexyloxycarbonylmethyl, cyclopropyl, cyclopentyl or cyclohexyl, each of which is optionally monosubstituted to trisubstituted by identical or different substituents from the series comprising methyl, methoxy, fluorine or chlorine, or represents oxetanylmethyl, oxetanylethyl, tetrahydrofuranylmethyl, tetrahydrofuranylethyl, tetrahydropyranylmethyl or tetrahydropyranylethyl, each of which is optionally substituted by methyl and/or ethyl, or represents benzyl or phenylethyl, each of which is optionally monosubstituted to trisubstituted by identical or different substituents, suitable substituents in each case being: fluorine, chlorine, bromine, cyano, nitro, methyl, ethyl, n- or i-propyl, n-, i-, s- or t-butyl, methoxy, ethoxy, n- or i-propoxy, methylthio, ethylthio, methoxycarbonyl, ethoxycarbonyl, trifluoromethyl, trifluoromethoxy or trifluoromethylthio, R⁴ and R⁵ independently of one another in each case represent hydrogen, methyl, ethyl or n- or i-propyl, R⁶ and R⁷ independently of one another in each case represent hydrogen, methyl, ethyl or n- or i-propyl or together represent a divalent alkanediyl radical having 2 to 5 carbon atoms, R⁸ represents hydrogen, methyl, ethyl or n- or i-propyl, or represents phenyl which is optionally monosubstituted to trisubstituted by identical or different substituents, suitable substituents being: fluorine, chlorine, bromine, cyano, nitro, methyl, ethyl, n- or i-propyl, n-, i-, s- or t-butyl, methoxy, ethoxy, n- or i-propoxy, methylthio, trifluoromethyl, trifluoromethoxy or trifluoromethylthio, R⁹ represents hydrogen, fluorine, chlorine, bromine, methyl, ethyl, n- or i-propyl, n-, i-, s- or t-butyl, fluoromethyl, difluoromethyl, trifluoromethyl, chloromethyl, dichloromethyl, trichloromethyl, difluorochloromethyl or dichlorofluoromethyl, and R¹⁰ represents hydrogen, methyl, ethyl, n- or i-propyl, n-, i-, s- or t-butyl, fluoromethyl, difluoromethyl, trifluoromethyl, chloromethyl, dichloromethyl, trichloromethyl, difluorochloromethyl or dichlorofluoromethyl, or R⁹ and R¹⁰ together represent a 1,3-propanediyl radical, a 1,4-butanediyl radical or a 1,5-pentanediyl radical, R¹¹ represents hydrogen, fluorine, chlorine, bromine, methyl, ethyl, n- or i-propyl, n-, i-, s- or t-butyl, fluoromethyl, difluoromethyl, trifluoromethyl, chloromethyl, dichloromethyl, trichloromethyl, difluorochloromethyl or dichlorofluoromethyl, R¹² represents hydrogen, methyl, ethyl, n- or i-propyl or n-, i-, s- or t-butyl, or methyl, ethyl or t-butyl, each of which is monosubstituted, disubstituted or trisubstituted by fluorine and/or chlorine, or represents allyl, n- or i-butenyl, chloroallyl, dichloroallyl, propargyl, chloropropargyl or methoxymethyl, or represents cyclopropyl, cyclopentyl or cyclohexyl, each of which is optionally monosubstituted to pentasubstituted by identical or different substituents from the series comprising fluorine, chlorine, methyl and/or methoxy, X¹ represents oxygen, a CH₂ group or an —N-group,
|
R⁸

X² represents nitrogen or a CH group, and
Z¹ represents oxygen or sulphur.

In all instances Het is particularly preferably

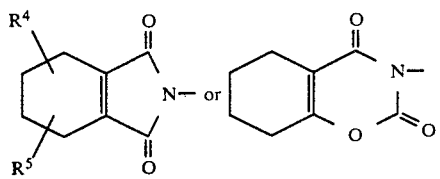

$R^4$ and $R^5$ representing hydrogen or methyl.

$R^1$ in the general formulae preferably represents fluorine.

$R^2$ in the general formulae preferably represents hydrogen.

$R^3$ in the general formulae preferably represents hydrogen, propargyl, cyanomethyl, cyanoethyl, methylsulphonyl, ethylsulphonyl, methoxycarbonyl or methoxyethoxycarbonyl.

If, for example, 3,4,5,6-tetrahydrophthalic anhydride and 6-amino-7-fluoro-4-propargyl-3H-1,4-benzoxazin-2(4H)-one are used as starting substances, the course of the reaction of process (a) according to the invention may be represented by the following equation:

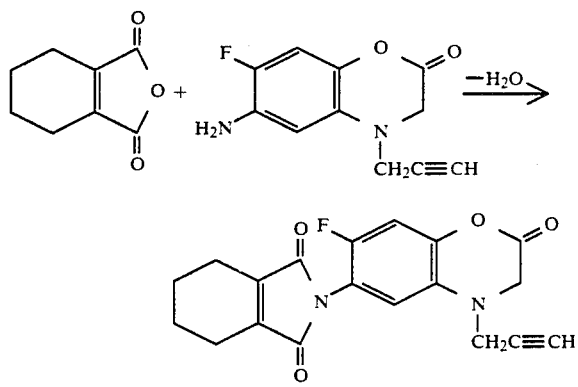

If, for example, ethyl 2-piperidinylcarboxylate and 4-propargyl-3H-1,4-benzoxazin-2(4H)-on-6-yl isocyanate are used as starting substances, the course of the reaction of process (b) according to the invention may be represented by the following equation:

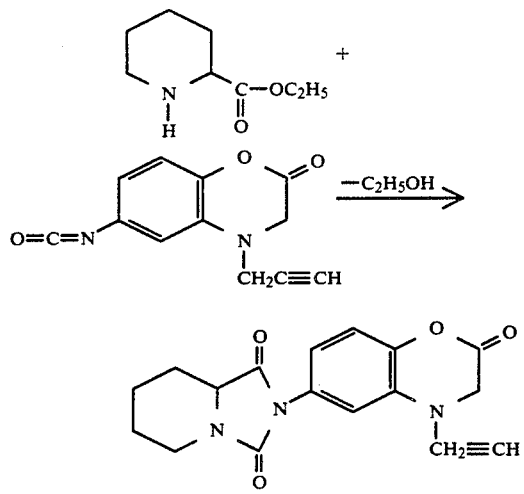

If, for example, 2,2-dimethyl-4,5,6,7,8-hexahydrocyclohexa-1,3-dioxin-4-one and 4-propargyl-3H-1,4-benzoxazin-2(4H)-on-6-yl isocyanate are used as starting substances, the course of the reaction of process (c) according to the invention may be represented by the following equation:

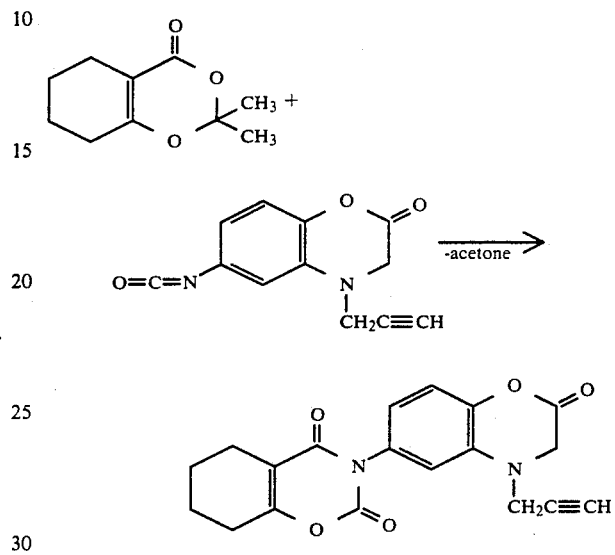

If, for example, 7-fluoro-3H-1,4-benzoxazin-2(4H)-on-6-yl-hydrazine and acetylacetone are used as starting substances, the course of the reaction of process (d) according to the invention may be represented by the following equation:

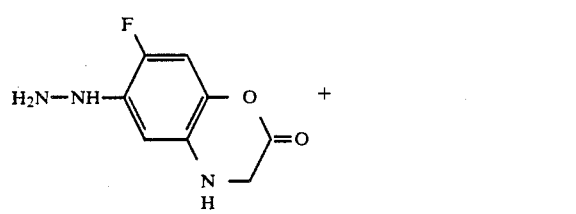

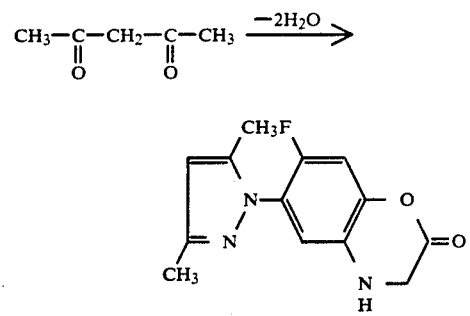

If for example, 6-(3,5-dimethylpyrazol-1-yl)-4-propargyl-7-fluoro-3H-1,4-benzoxazin-2(4H)-one is used as the starting compound and sulphuryl chloride as the halogenating agent, the course of the reaction of process (e) according to the invention may be represented by the following equation:

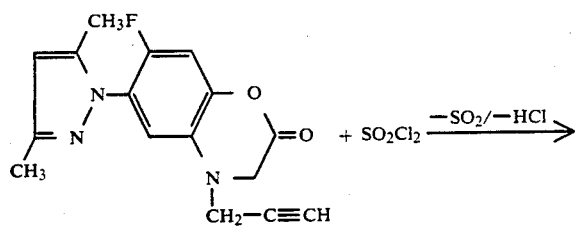

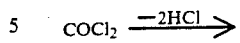

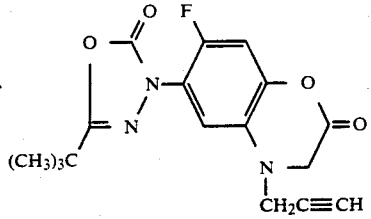

If, for example, (7-fluoro-4-propargyl-3H-1,4-benzoxazin-2-(4H)-on-6-yl)-4H-pyrzolin-5-one is used as the starting compound and phosphorus oxychloride in the presence of triphenylphosphane as the halogenating agent, the course of the reaction of process (f) according to the invention may be represented by the following equation:

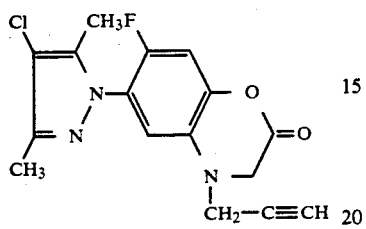

If, for example, 7-fluoro-3H-1,4-benzoxazin-2(4)-on-6-yl)-hydrazine and ethyl N-ethoxycarbonyl-2,2-dimethylpropaneimidate are used as starting substances, the course of the reaction of process (h) according to the invention may be represented by the following equation:

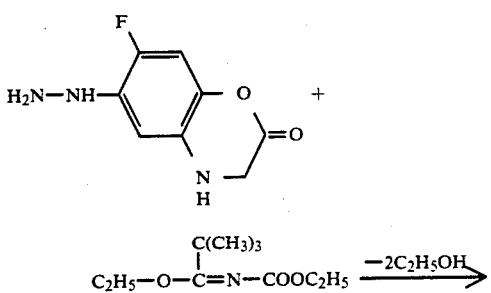

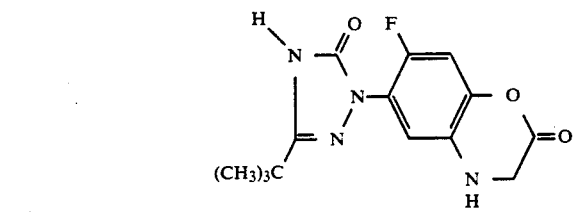

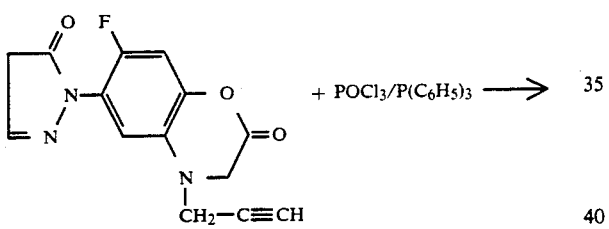

If, for example, N-pivaloyl-N'-(7-fluoro-4-propargyl-3H-1,4-benzoxazin-2(4)-on-6-yl)-hydrazine is used as the starting compound, the course of the reaction of process (g) according to the invention may be represented by the following equation:

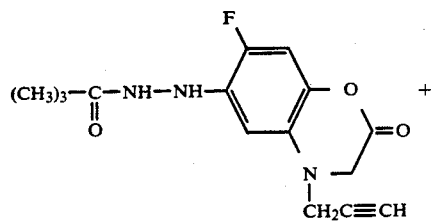

If, for example, (7-fluoro-4-propargyl-3H-1,4-benzoxazin-2(4)-on-6-yl)-3-t-butyl-4H-1,2,4-triazolin-5-one and methyl iodide are used as starting substances, the course of the reaction of process (i) according to the invention may be represented by the following equation:

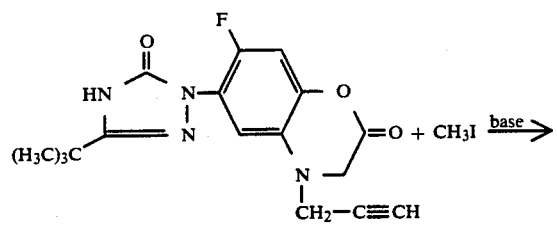

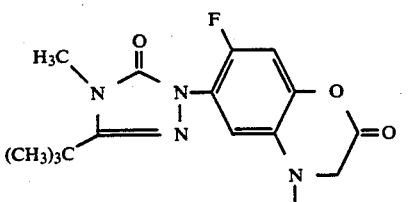

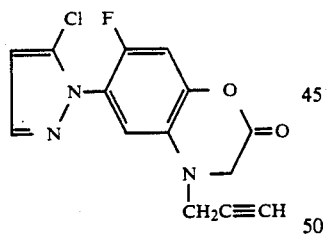

If, for example, piperidin-2one-(7-fluoro-4-methyl-3H-1,4-benzoxazin-2(4)-on-6-yl)-hydrazone is used as the starting compound, the course of the reaction of process (j) according to the invention may be represented by the following equation:

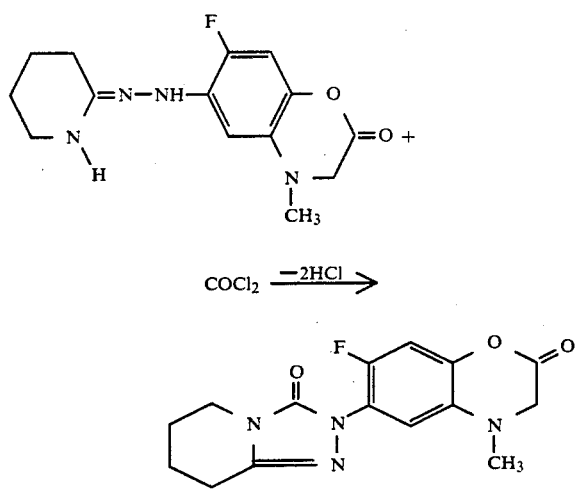

If, for example, tetrahydro-hydroxy-isobenzofuran and 4-propargyl-3H-1,4-benzoxazin-2(4)-on-6-yl)-hydrazine are used as the starting compounds, the course of the reaction of process (k) according to the invention may be represented by the following equation:

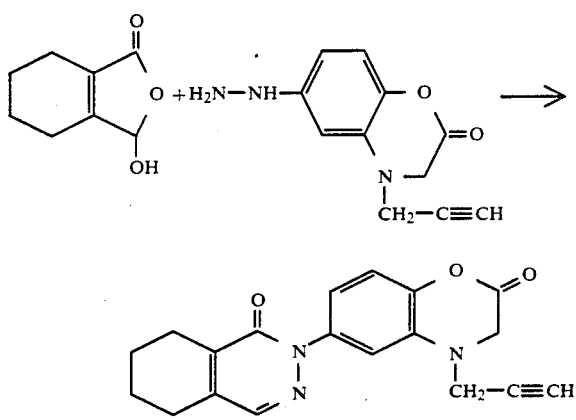

If, for example, (7-fluoro-3H-1,4-benzoxazin-2(4)-on-6-yl)-3-t-butyl-4-methyl-4H-1,2,4-triazolin-5-one and propargyl bromide are used as the starting substances, the course of the reaction of process (l) according to the invention may be represented by the following equation:

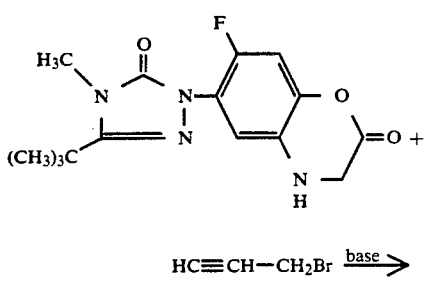

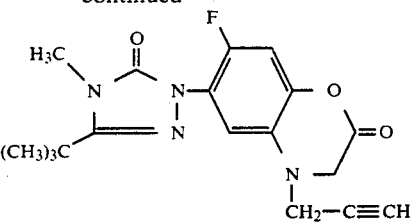

The anhydrides of the formula (II) required as starting substances for carrying out process (a) according to the invention are known or can be obtained in analogy to known processes (cf., for example, Gazz. chim. Ital. 57, 300-311 [1927]; DE-OS (German Published Specification) 3,644,222; J. Org. Chem. 51, 4150-4158 [1986]; Tetrahedron Lett. 25, 6027-6030 [1984]; J. Org. Chem. 42, 4162-4164 [1977]; Liebigs Ann. Chem. 1977, 772-790; Tetrahedron 25, 4099-4108 [1969]; JP 43/9046).

The aminobenzoxazinones of the formula (III) which are furthermore required as starting substances for carrying out process (a) according to the invention were hitherto unknown and are likewise a subject of the invention.

They are obtained when 2-nitrophenols of the formula (XVII)

in which $R^1$ represents hydrogen or halogen, are reacted in a first step with derivatives of the glycolyl chloride of the general formula

in which $E^1$ represents an electron-attracting leaving group, in the presence of a diluent such as, for example, toluene, and if appropriate in the presence of a reaction auxiliary such as, for example, triethylamine, at temperatures between −30° C. and 120° C., and the resulting glycolic esters of the formula (XIX)

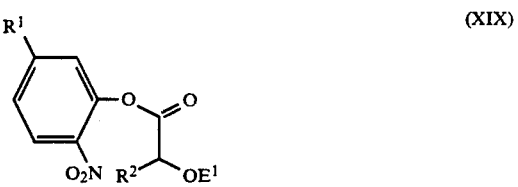

are reduced in a second step either with molecular hydrogen in the presence of a noble metal catalyst such as, for example, Pd/C, in a diluent such as, for example, tetrahydrofuran, and the product is subsequently cyclized under acid catalysis, or they are cyclized directly in dilute acid, such as, for example, acetic acid, under reductive conditions at temperatures between 20° and 150° C.

The resulting benzoxazinones of the formula (XX)

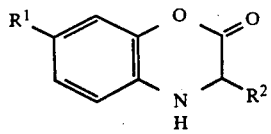

are then nitrated in a customary manner using nitric acid in sulphuric acid, and the product is subsequently reduced, likewise in a generally customary manner, using a reactant such as, for example, iron in acetic acid.

The carboxylic esters of the formula (IV) required as starting substances for carrying out process (b) are generally known compounds of organic chemistry or can be obtained in analogy to known processes (cf., for example, U.S. Pat. No. 4,730,006. Pestic. Sci. 16, 277–286 [1985]; Chem. Pharm. Bull. 32, 3934–3944 [1984]; Liebigs Ann. Chem. 1983, 1133–1151; Synthesis 1981, 915–917; Tetrahedron Lett. 22, 2485–2486 [1981]; Chem. Ber. 111, 1058–1076 [1978]; Angew. Chem. 89, 344–345 [1977]; Chem. Ber. 110, 942–947 [1977]; Chem. Lett. 1976, 1095–1096; Angew. Chem. 88, 295–296 [1976]; DE 2,058,012; Bull. chem. Soc. Japan 44, 474–477 [1971]; J. chem. Soc. Perkin I. 1987, 877–884; DE 3,702,943; DE 2,331,549;. J. Heterocycl. Chem. 6, 181–185, [1969]).

In this formula (IV), $R^{15}$ preferably represents a radical of the formula

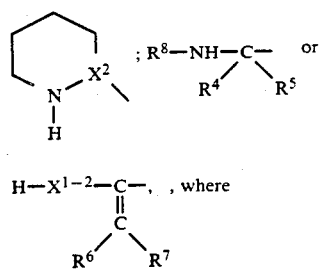

$X^{1-2}$ represents oxygen or a

group and $R^{16}$ preferably represents straight-chain or branched alkyl having 1 to 4 carbon atoms, in particular methyl or ethyl.

The iso(thio)cyanates of the formula (V) or (Va) furthermore required for carrying out process (b) or (c) can be obtained in analogy to known processes (cf., for example, FR 2,003,438; ZA 67/3761 or CA70: 67 955d; EP-A 105,991; EP-A 67,689 or GB 1,336,871 and the Preparation Examples), for example when amines of the formula (III)

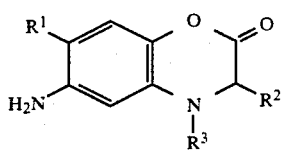

in which $R^3$ has the abovementioned meaning with the exception of hydrogen, are reacted with phosgene, thiophosgene or diphosgene ($Cl_3C$—O—CO—Cl), if appropriate in the presence of a diluent, such as, for example, toluene, at temperatures between 20° C. and 120° C.

The compounds of the formula (VIa) or (VIb) required as starting substances for carrying out process (c) are generally known compounds and can be prepared by processes known per se (cf. Chem. Ber. 105 (1972), 137–149; J. Am. Chem. Soc. 74 (1952), 6305–6406; loc. cit. 75 (1953), 5400–5402; DE-OS (German Published Specification) 1,957,312).

The phenylhydrazines of the formula (VII) required as starting substances for carrying out processes (d), (h) and (k) were hitherto unknown and are likewise a subject of the present invention.

In formula (VII), $R^{9-1}$ and $R^{10-1}$ independently of one another preferably represent hydrogen, $C_1$-$C_6$-alkyl or halogeno-$C_1$-$C_4$-alkyl, in particular hydrogen, methyl, ethyl, n- or iso-propyl, n-, iso-, sec.- or tert-butyl or halogenomethyl having 1 to 3 identical or different halogen atoms, or $R^{9-1}$ and $R^{10-1}$ together represent a divalent alkanediyl radical having preferably 2 to 6 carbon atoms, in particular a 1,3-propanediyl radical, a 1,4-butanediyl radical or a 1,5-pentanediyl radical.

The phenylhydrazines of the formula (VII) are obtained when amino-benzoxazinones of the formula (III)

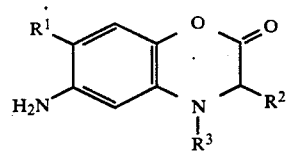

are initially diazotized in a customary manner using sodium nitrite in the presence of an acid, such as, for example, hydrochloric acid, and the product is subsequently reduced, likewise in a generally customary manner, using a reducing agent such as, for example, tin(II) chloride.

The compounds of the formula (III) and (VII) may be named together in a joint formula (IIIa):

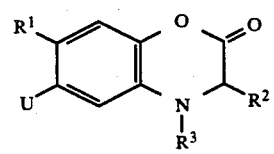

in which

U represents —$NH_2$ or —NH—$NH_2$.

The 1,3-diketones of the formula (VIII) which are furthermore required as starting substances for carrying out process (d), and derivatives of these diketones, such as, for example, enol ethers, enol esters, ketals, enol ether ketals, enamines or β-halogenovinyl ketones, are generally known compounds of organic chemistry.

In formula (VIII), $R^{11-1}$ preferably represents hydrogen, $C_1$–$C_6$-alkyl or halogeno-$C_1$–$C_4$-alkyl, in particular hydrogen, methyl, ethyl, n- or iso-propyl, n-, iso-, sec.- or tert.-butyl, or halogenomethyl having 1 to 3 identical or different halogen atoms, in particular fluorine or chlorine.

The nitrogen-containing N-aryl-heterocycles of the formula (If) required as starting substances for carrying out process (e) are compounds according to the invention and can be obtained with the aid of processes (d) and (l) according to the invention.

The N-aryl-pyrazolinones of the formula (IX) required as starting substances for carrying out process (f) according to the invention were hitherto unknown and are likewise a subject of the present invention.

They are obtained when β-ketoesters of the formula (XXI)

in which

R represents alkyl, in particular methyl or ethyl, are reacted with phenylhydrazines of the formula (VII)

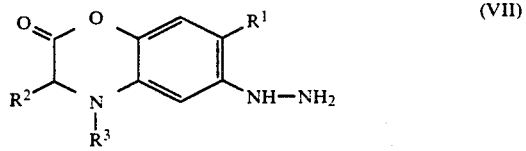

if appropriate in the presence of a diluent, such as, for example, ethanol, and if appropriate in the presence of a reaction auxiliary, such as, for example, sulphuric acid, at temperatures between 20° C. and 120° C.

The β-ketoesters of the formula (XXI) are generally known compounds of organic chemistry.

The phenyl hydrazides of the formula (X) required as starting substances for carrying out process (g) were hitherto unknown and are likewise a subject of the present invention.

They are obtained when phenylhydrazines, of the formula (XII)

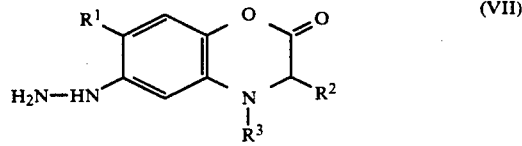

are reacted with acylating agents of the formula (XXII)

in which $E^3$ represents an electron-attracting leaving group, preferably halogen, or represents a radical

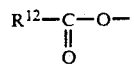

where $R^{12}$ has the abovementioned meaning and represents, in particular, chlorine, if appropriate in the presence of a diluent, such as, for example, dichloromethane, and if appropriate in the presence of a reaction auxiliary, such as, for example, triethylamine, at temperatures between −20° C. and +60° C.

Acylating agents of the formula (XXII) are generally known compounds of organic chemistry.

The iminocarboxylic esters of the formula (XI) required as starting substances for carrying out process (h) are known or can be obtained in analogy to known processes (cf., for example, Chem. Ber. 119, 2444-2457 [1986]; Bull. chem. Soc. Jpn. 55, 3943-3944 [1982]; Chem. Lett. 1982, 1015-1016; Chem. Lett. 1978, 1403-1404; J. Amer. Chem. Soc. 95, 3957-3963 [1973]; J. Org. Chem. 36, 3251-3252 [1971].

In formula (XI), $R^{18}$ and $R^{19}$ independently of one another preferably represent $C_1$–$C_4$-alkyl, in particular methyl or ethyl.

The nitrogen-containing N-aryl-heterocycles of the formula (Ii) required as starting substances for carrying out process (i) are compounds according to the invention and can be obtained with the aid of process (h) according to the invention.

The alkylating agents of the formula (XII) furthermore required as starting substances are generally known compounds of organic chemistry.

In formula (XII), $R^{14-1}$ preferably represents $C_1$–$C_6$-alkyl, $C_3$–$C_6$-alkenyl, $C_3$–$C_6$-alkynyl, halogeno-$C_1$–$C_4$-alkyl having 1 to 9 identical or different halogen atoms, halogeno-$C_3$–$C_6$-alkenyl having 1 to 5 identical or different halogen atoms, or halogeno-$C_3$–$C_6$-alkynyl having 1 to 5 identical or different halogen atoms $R^{14-1}$ in particular represents methyl, ethyl, n- or i-propyl or n-, i-, s- or t-butyl, or represents methyl, ethyl or t-butyl, each of which is monosubstituted, disubstituted or trisubstituted by fluorine and/or chlorine, or represents allyl, n- or i-butenyl, chloroallyl, dichloroallyl, propargyl or chloropropargyl.

$E^1$ preferably represents halogen, in particular chlorine, bromine or iodine, or represents in each case optionally substituted alkylsulphonyloxy, alkoxysulphonyloxy or arylsulphonyloxy, such as, for example, methanesulphonyloxy, trifluoromethanesulphonyloxy, methoxysulphonyloxy, ethoxysulphonyloxy or p-toluenesulphonyloxy.

The amidrazones of the formula (XIII) required as starting substances for carrying out process (j) 1 according to the invention were hitherto unknown.

$R^{13-1}$ and $R^{14-2}$ together represent, preferably, a divalent alkanediyl radical having 2 to 6 carbon atoms, in particular a 1,3-propanediyl radical, a 1,4-butanediyl radical or a 1,5-pentanediyl radical.

The amidrazones of the formula (XIII) are obtained in analogy to known processes (cf., for example, U.S. Pat. No. 4,080,192 or DE-OS (German Published Specification) 1,957,783) when lactams of the formula (XXIII)

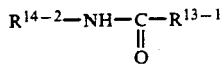

$$R^{14-2}-NH-\underset{\underset{O}{\|}}{C}-R^{13-1} \qquad \text{(XXIII)}$$

are reacted, in a first step, with a halogenating agent, such as, for example, phosphorus oxychloride, thionyl chloride or phosgene, if appropriate in the presence of a diluent, such as, for example, ethanol or dioxane, and if appropriate in the presence of a reaction auxiliary, such as, for example triethylamine or pyridine, at temperatures between 0° C. and 50° C., and the resulting chloroimides of the formula (XXIV)

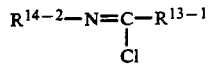

$$R^{14-2}-N=\underset{\underset{Cl}{|}}{C}-R^{13-1} \qquad \text{(XXIV)}$$

are reacted with phenylhydrazines of the formula (VII)

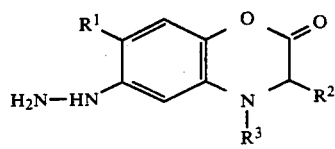

if appropriate in the presence of a diluent, such as, for example, ethanol, and if appropriate in the presence of a reaction auxiliary, such as, for example, triethylamine or pyridine, at temperatures between 0° C. and 80° C.

Lactams of the formula (XXIII) are generally known compounds of organic chemistry.

Hydroxyisobenzofuranone, of the formula (XIV), which is required as a starting substance for carrying out process (k) according to the invention, is a generally known compound of organic chemistry.

The nitrogen-containing N-aryl-heterocycles of the formula (In) required as starting substances for carrying out process (1) are compounds according to the invention and can be obtained with the aid of processes (a) to (k) according to the invention.

The alkylating or acylating agents of the formula (XVI) which are furthermore required are known compounds of organic chemistry. Ez preferably represents halogen, in particular chlorine, bromine or iodine, or represents in each case optionally substituted alkylsulphonyloxy having preferably 1 to 4 carbon atoms, alkoxysulphonyloxy having preferably 1 to 4 carbon atoms or arylsulphonyloxy having preferably 6 to 10 carbon atoms, such as, in particular, methanesulphonyloxy, trifluoromethanesulphonyloxy, methoxysulphonyloxy, ethoxysulphon-yloxy or p-toluenesulphonyloxy.

Suitable diluents for carrying out process (a) according to the invention are inert organic solvents These include, in particular, aliphatic, alicyclic or aromatic, optionally halogenated hydrocarbons, such as, for example, benzine, benzene, toluene, xylene, chlorobenzene, petroleum ether, hexane, cyclohexane, dichloromethane, chloroform or carbon tetrachloride, ethers, such as diethyl ether, dioxane, tetrahydrofuran, ethylene glycol dimethyl ether or ethylene glycol diethyl ether, ketones, such as acetone or butanone, nitriles, such as acetonitrile or propionitrile, amides, such as dimethylformamide, dimethylacetamide, N-methylformanilide, N-methylpyrrolidone or hexamethylphosphoric triamide, esters, such as ethyl acetate, sulphoxides, such as dimethyl sulphoxide, or carboxylic acids, such as acetic acid or propionic acid.

If appropriate, process (a) according to the invention can be carried out in the presence of a suitable reaction auxiliary. Auxiliaries which are preferably used are inorganic or organic acids, such as, for example, acetic acid or p-toluenesulphonic acid, anhydrides, such as, for example, acetic anhydride, or acid chlorides, such as acetyl chloride. It is also possible to use other customary water-eliminating agents, such as, for example, N,N'-dicyclohexylcarbodiimide, or customary acylation catalysts, such as, for example, 4-(N,N-dimethylamino)-pyridine, as reaction auxiliaries.

When carrying out process (a) according to the invention, the reaction temperatures can be varied within a substantial range. In general, the process is carried out at temperatures between 20° C. and 180° C., preferably at temperatures between 50° C. and 150° C.

For carrying out process (a) according to the invention, 1 to 1.5 moles, preferably 1 to 1.2 moles, of aminobenzoxazinone of the formula (III) and if appropriate 0.01 to 1.2 moles, preferably 0.1 to 1 mole, of reaction auxiliary are generally employed per mole of anhydride of the formula (II). The reaction is carried out and the reaction products are worked up and isolated by generally customary methods (cf. also the Preparation Examples).

Suitable diluents for carrying out process (b) according to the invention are inert inorganic solvents. These include, in particular, aliphatic, alicyclic or aromatic, optionally halogenated hydrocarbons, such as, for example, benzine, benzene, toluene, xylene, chlorobenzene, dichlorobenzene, petroleum ether, hexane, cyclohexane, dichloromethane, chloroform and carbon tetrachloride, ethers, such as diethyl ether, dioxane, tetrahydrofuran or ethylene glycol dimethyl ether or ethylene glycol diethyl ether, nitriles, such as acetonitrile or propionitrile, amides, such as dimethylformamide, dimethylacetamide, N-methylformanilide, N-methylpyrrolidone or hexamethylphosphoric triamide, or alcohols, such as methanol, ethanol or propanol.

If appropriate, process (b) according to the invention is carried out in the presence of a suitable reaction auxiliary. Suitable reaction auxiliaries are all customary inorganic or organic bases. These include, for example, alkali metal hydroxides, such as sodium hydroxide or potassium hydroxide, alkali metal carbonates, such as sodium carbonate, potassium carbonate or sodium hydrogen carbonate, and also tertiary amines, such as triethylamine, N,N-dimethylaniline, pyridine, N,N-dimethylaminopyridine, diazabicyclooctane (DABCO), diazabicyclononene (DBN) or diazabicycloundecene (DBU).

When carrying out process (b) according to the invention, the reaction temperatures can be varied within a substantial range. In general, the process is carried out at temperatures between 0° C. and 150° C., preferably at temperatures between 20° C. and 120° C.

For carrying out process (b) according to the invention, 0.5 to 5 moles, preferably 0.8 to 1.5 moles, of iso(-thio)cyanate of the formula (V) and if appropriate 1 to 10 moles, preferably 1 to 5 moles, of reaction auxiliary are generally employed per mole of carboxylic ester of the formula (IV) or of a corresponding acid addition salt. It is also possible here to prepare the iso(thio)cyanates of the formula (V) in a preceding reaction directly in the reaction vessel from amines of the formula (III)

and phosgene, thiophosgene or diphosgene (Cl₃C—O—CO—Cl), and to react the products further with the carboxylic esters of the formula (IV) without isolation in a "one-pot process".

The reaction is carried out and the reaction products are worked up and isolated by generally customary methods (cf. also the Preparation Examples).

If appropriate, process (c) according to the invention is carried out using diluents. Suitable diluents are preferably high-boiling, inert organic solvents. These mainly include optionally halogenated hydrocarbons, such as decalin, tetralin, toluene, xylene, furthermore chlorobenzene and 1,2-dichlorobenzene, and also mesitylene.

In process (c) according to the invention, the reaction temperatures can be varied over a substantial range. In general, the process is carried out at temperatures between 80° C. and 250° C., preferably at temperatures between 120° C. and 220° C.

Process (c) according to the invention is generally carried out under atmospheric pressure. However, it is also possible to carry out the process under elevated or reduced pressure.

For carrying out process (c) according to the invention, the specifically required starting substances are generally employed in approximately equimolar amounts. However, it is also possible to use one of the two specifically employed components in a substantial excess. In general, the reactions are carried out in a suitable diluent—however, if appropriate, also without a diluent—and the reaction mixture is stirred at the specifically required temperature. Working-up in process (c) according to the invention is carried out in each case by customary methods.

Suitable diluents for carrying out processes (d) and (k) according to the invention are inert organic solvents. These include, in particular, aliphatic or aromatic, optionally halogenated hydrocarbons, such as, for example, benzine, benzene, toluene, xylene, chlorobenzene, petroleum ether, hexane, cyclohexane, dichloromethane, chloroform and carbon tetrachloride, ethers, such as diethyl ether, dioxane, tetrahydrofuran, ethylene glycol dimethyl ether or ethylene glycol diethyl ether, nitriles, such as acetonitrile or propionitrile, amides, such as dimethylformamide, dimethylacetamide, N-methylformanilide, N-methylpyrrolidone or hexamethylphosphoric triamide, esters, such as ethyl acetate, sulphoxides, such as dimethyl sulphoxide, alcohols, such as methanol, ethanol or propanol, or acids, such as acetic acid.

If appropriate, processes (d) and (k) according to the invention are carried out in the presence of a suitable reaction auxiliary. Suitable reaction auxiliaries are, in particular, inorganic mineral acids, such as, for example, hydrochloric acid or sulphuric acid. It is also possible to employ the phenylhydrazines of the formula (VII) which are suitable as starting substances in the form of corresponding acid addition salts, such as, for example, hydrochlorides.

When carrying out processes (d) and (k) according to the invention, the reaction temperatures can be varied over a substantial range. In general, the processes are carried out at temperatures between −20° C. and 180° C., preferably at temperatures between 20° C. and 120° C.

For carrying out processes (d) and (k) according to the invention, 0.5 to 10 moles of 1,3-diketone of the formula (VIII) or of a corresponding derivative, or hydroxyisobenzofuranone of the formula (XIV), and if appropriate 0.01 to 1 mole of reaction auxiliary are generally employed per mole of phenylhydrazine of the formula (II), or of a corresponding acid addition salt. The reaction is carried out and the nitrogen-containing N-aryl-heterocycles of the formula (Id) or (II) are worked up and isolated by generally customary methods (cf. also the Preparation Examples).

If 1,3-diketones of the formula formula (VIII) are used in which the substituent $R^{10}$ differs from the substituent $R^{11\text{-}1}$, the result is, as a rule, mixtures of isomers of compounds of the formula (Id-1)

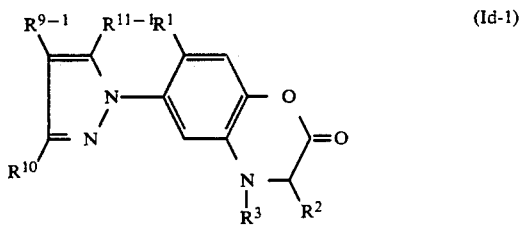

and compounds of the formula (Id-2)

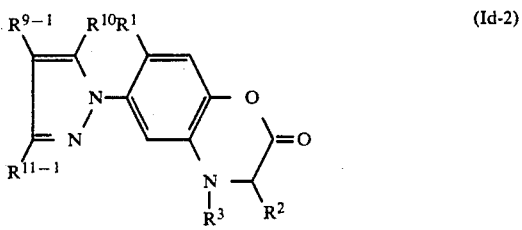

The desired reaction products of the formula (Id) may be isolated from these mixtures of isomers by customary separation processes (distillation, crystallization, chromatography).

Suitable halogenating agents for carrying out process (e) according to the invention are customary halogenating agents. Sulphuryl chloride, elemental chlorine or elemental bromine are particularly preferably used as halogenating agents.

Suitable diluents for carrying out process (e) according to the invention are inert organic solvents. These include, in particular, aliphatic, alicyclic or aromatic, optionally halogenated hydrocarbons, such as, for example, benzine, benzene, toluene, xylene, chlorobenzene, o-dichlorobenzene, petroleum ether, hexane, cyclohexane, dichloromethane, chloroform or carbon tetrachloride.

When carrying out process (e) according to the invention, the reaction temperatures can be varied over a substantial range. In general, the process is carried out at temperatures between 0° C. and 150° C., preferably at temperatures between 35° C. and 70° C.

For carrying out process (e) according to the invention, 1 to 5 moles, preferably 1 to 2 moles, of halogenating agent are generally employed per mole of nitrogen-containing N-aryl-heterocycle of the formula (Ie).

The reaction is carried out and the reaction products are worked up and isolated by generally customary methods (cf. also the Preparation Examples).

Suitable halogenating agents for carrying out process (f) according to the invention are likewise customary halogenating agents. Inorganic acid halides, such as, for example, phosphorus oxychloride, thionyl chloride, phosgene, phosphorus tribromide or diphosgene (Cl₃C—O—CO—Cl) are particularly preferably used.

Suitable diluents for carrying out process (f) according to the invention are inert organic solvents These include, in particular, aliphatic, alicyclic or aromatic, optionally halogenated hydrocarbons, such as, for example, benzine, benzene, toluene, xylene, chlorobenzene, o-dichlorobenzene, petroleum ether, hexane, cyclohexane, dichloromethane, chloroform or carbon tetrachloride, or basic diluents, such as, for example, pyridine. It is also possible to use an appropriate excess of halogenating agent simultaneously as the diluent.

Process (f) according to the invention is preferably carried out in the presence of a suitable reaction auxiliary. Suitable reaction auxiliaries are, in particular, customary auxiliary nucleophiles, such as, for example, triphenylphosphine, dimethylaniline or dimethylformamide.

When carrying out process (f) according to the invention, the reaction temperatures can be varied over a substantial range. In general, the process is carried out at temperatures between 0° C. and 200° C., preferably at temperatures between 30° C. and 150° C.

For carrying out process (f) according to the invention, 1 to 10 moles, preferably 1 to 5 moles, of halogenating agent and if appropriate 0.01 to 1 mole, preferably 0.05 to 0.1 mole, of reaction auxiliary are generally employed per mole of N-arylpyrazolinone of the formula (IX).

The reaction is carried out and the reaction products are worked up and isolated by generally customary methods (cf. also the Preparation Examples).

Suitable diluents for carrying out processes (g) and (j) according to the invention are inert organic solvents. These include, in particular, aliphatic, alicyclic or aromatic, optionally, halogenated hydrocarbons, such as, for example, benzine, benzene, toluene, xylene, chlorobenzene, o-dichlorobenzene, petroleum ether, hexane, cyclohexane, dichloromethane, chloroform or carbon tetrachloride.

Processes (g) and (j) according to the invention are preferably carried out in the presence of a suitable reaction auxiliary. Suitable reaction auxiliaries are all customary bases. Tertiary amines, such as triethylamine, N,N-dimethylaniline, pyridine, N,N-dimethylaminopyridine, diazabicyclooctane (DABCO), diazabicyclononene (DBN) or diazabicycloundecene (DBU) are particularly preferably used.

When carrying out process (g) and (j) according to the invention, the reaction temperatures can be varied over a substantial range. In general, the processes are carried out at temperatures between −20° C. and 180° C., preferably at temperatures between 0° C. and 150° C.

For carrying out process (j) according to the invention, 1 to 5 moles, preferably 1 to 1.5 moles, of phosgene and if appropriate 1 to 5 moles, preferably 1 to 3 moles, of reaction auxiliary are generally employed per mole of amidrazone of the formula (XIII).

The reaction is carried out and the reaction products are worked up and isolated by generally customary methods.

For carrying out process (g) according to the invention, 1 to 5 moles, preferably 1 to 1.5 moles, of phosgene and if appropriate 1 to 5 moles, preferably 1.0 to 3.0 moles, of reaction auxiliary are generally employed per mole of phenyl hydrazide, of the formula (X).

The reaction is carried out and the reaction products are worked up and isolated by generally customary methods (cf. also the Preparation Examples).

Suitable diluents for carrying out process (h) according to the invention are inert organic solvents. These include, in particular, alihatic, alicyclic or aromatic, optionally halogenated hydrocarbons, such as, for example, benzine, benzene, toluene, xylene, chlorobenzene, petroleum ether, hexane, cyclohexane, dichloromethane, chloroform and carbon tetrachloride, or ethers, such as diethyl ether, dioxane, tetrahydrofuran, ethylene glycol dimethyl ether or ethylene glycol diethyl ether, ketones, such as acetone or butanone, nitriles, such as acetonitrile or propionitrile, amides, such as dimethylformamide, dimethylacetamide, N-methylformanilide, N-methylpyrrolidone or hexamethylphosphoric triamide, esters, such as ethyl acetate, sulphoxides, such as dimethyl sulphoxide, or alcohols, such as methanol, ethanol or propanol.

When carrying out process (h) according to the invention, the reaction temperatures can be varied over a substantial range. In general, the process is carried out at temperatures between 0° C. and 180° C., preferably at temperatures between 50° C. and 150° C.

For carrying out process (h) according to the invention, 1 to 3 moles, preferably 1 to 2 moles, of iminocarboxylic ester of the formula (XI) are generally employed per mole of phenylhydrazine of the formula (VII).

The reaction is carried out, and the reaction products are worked up and isolated by generally customary methods (cf. also the Preparation Examples).

Suitable diluents for carrying out process (i) according to the invention are inert organic solvents The following are preferably used: aliphatic, cyclic or aromatic, optionally halogenated hydrocarbons, such as, for example, benzine, benzene, toluene, xylene, pentane, hexane, heptane, cyclohexane, petroleum ether, ligroin, methylene chloride, chloroform, carbon tetrachloride, chlorobenzene or dichlorobenzene, ethers, such as diethyl ether, diisopropyl ether, dioxane, tetrahydrofuran, ethylene glycol diethyl ether or ethylene glycol dimethyl ether, ketones, such as acetone, butanone, methyl isopropyl ketone or methyl isobutyl ketone, esters, such as ethyl acetate, nitriles, such as acetonitrile or propionitrile, or amides, such as dimethylformamide, dimethylacetamide, N-methylpyrrolidone or hexamethylphosphoric triamide. If alkylating agents of the formula (XII) are used in liquid form, it is also possible to employ these simultaneously as the diluent, in appropriate excess.

Suitable reaction auxiliaries for carrying out process (i) according to the invention are all inorganic and organic bases which can customarily be used. The following are preferably used: alkali metal hydrides, alkali metal hydroxides, alkali metal amides, alkali metal carbonates or alkali metal hydrogen carbonates, such as, for example, sodium hydride, sodium amide, sodium hydroxide, sodium carbonate, potassium carbonate or sodium hydrogen carbonate, and also tertiary amines, such as, for example, triethylamine, N,N-dimethylaniline, pyridine, 4-(N,N-dimethylamino)-pyridine, diazabicyclooctane (DABCO), diazabicyclononene (DBN) or diazabicycloundecene (DBU).

When carrying out preparation process (i), the reaction temperatures can be varied over a substantial range. In general, the process is carried out between −20° C. and +150° C., preferably between 0° C. and +100° C.

For carrying out process (i) according to the invention, 1 to 15 moles, preferably 1 to 5 moles, of alkylating agent of the formula (XII) and if appropriate 1 to 3 moles, preferably 1 to 2 moles, of reaction auxiliary are generally employed per mole of nitrogen-containing N-aryl-heterocycle of the formula (Ii).

The reaction is carried out and the reaction products are worked up and isolated by generally customary methods (cf. also the Preparation Examples).

Suitable diluents for carrying out process (1) according to the invention are inert organic solvents The following are preferably used: aliphatic, alicyclic or aromatic, optionally halogenated hydrocarbons, such as, for example, benzine, benzene, toluene, xylene, pentane, hexane, heptane, cyclohexane, petroleum ether, ligroin, methylene chloride, chloroform, carbon tetrachloride, chlorobenzene or dichlorobenzene, ethers, such as diethyl ether, diisopropyl ether, dioxane, tetrahydrofuran, ethylene glycol diethyl ether or ethylene glycol dimethyl ether, ketones, such as acetone, butanone, methyl isopropyl ketone or methyl isobutyl ketone, esters, such as ethyl acetate, acids, such as acetic acid, nitriles, such as acetonitrile or propionitrile, or amides, such as dimethylformamide, dimethylacetamide, N-methylpyrrolidone or hexamethylphosphoric triamide. If alkylating agents of the formula (XVI) in liquid form are used as reactants, it is also possible to employ these simultaneously as the diluent, in appropriate excess.

Suitable reaction auxiliaries for carrying out process (1) according to the invention are all inorganic and organic bases which can customarily be used. The following are preferably used: alkali metal hydrides, alkali metal hydroxides, alkali metal amides, alkali metal carbonates or alkali metal hydrogen carbonates, such as, for example, sodium hydride, sodium amide, sodium hydroxide, sodium carbonate or sodium hydrogen carbonate, and also tertiary amines, such as, for. example, triethylamine, N,N-dimethylaniline, pyridine, 4-(N,N-dimethylamino)-pyridine,diazabicyclooctane(-DABCO), diazabicyclononene (DBN) or diazabicycloundecene (DBU).

When carrying out process (1) according to the invention, the reaction temperatures can be varied over a substantial range. In general, the process is carried out between −20° C. and +150° C., preferably between 0° C. and +100° C.

For carrying out process (1) according to the invention, 1 to 20 moles, preferably 1 to 15 moles, of alkylating or acylating agent of the formula (XVI) and if appropriate 1 to 3 mcles, preferably 1 to 2 moles, of reaction auxiliary are generally employed per mole of nitrogen-containing N-aryl-heterocycle of the formula (In).

The reaction is carried out and the reaction products of the formula (Im) are worked up and isolated by customary methods.

The active compounds according to the invention can be used as defoliants, desiccants, agents for destroying broad-leaved plants and, especially, as weed-killers. By weeds, in the broadest sense, there are to be understood all plants which grow in locations where they are undesired. Whether the substances according to the invention act as total or selective herbicides depends essentially on the amount used.

The active compounds according to the invention can be used, for example, in connection with the following plants:

Dicotyledon weeds of the oenera: Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver and Centaurea.

Dicotyledon cultures of the qenera: Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita.

Monocotyledon weeds of the genera: Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus and Apera.

Monocotyledon cultures of the cenera: Oryza, Zea, Triticum, Hordeum, Avena, Secale, Sorghum, Panicum, Saccharum, Ananas, Asparagus and Allium.

However, the use of the active compounds according to the invention is in no way restricted to these genera, but also extends in the same manner to other plants.

The compounds are suitable, depending on the concentration, for the total combating of weeds, for example on industrial terrain and rail tracks, and on paths and squares with or without tree plantings. Equally, the compounds can be employed for combating weeds in perennial cultures, for example afforestations, decorative tree plantings, orchards, vineyards, citrus groves, nut orchards, banana plantations, coffee plantations, tea plantations, rubber plantations, oil palm plantations, cocoa plantations, soft fruit plantings and hopfields, and for the selective combating of weeds in annual cultures.

The active substances of the formula (I) according to the invention are particularly suitable for selectively combating weeds of monocotyledon and dicotyledon weeds in monocotyledon and dicotyledon crops using the pre-emergence and post-emergence method.

The active compounds can be converted into the customary formulations, such as solutions, emulsions, wettable powders, suspensions, powders, dusting agents, pastes, soluble powders, granules, suspension-emulsion concentrates, natural and synthetic materials impregnated with active compound, and very fine capsules in polymeric substances.

These formulations are produced in a khown manner, for example by mixing the active compounds with extenders, that is liquid solvents and/or solid carriers, optionally with the use of surface-active agents, that is emulsifying agents and/or dispersing agents and/or foam-forming agents.

In the case of the use of water as an extender, organic solvents can, for example, also be used as auxiliary solvents. As liquid solvents, there are suitable in the main: aromatics, such as xylene, toluene or alkylnaphthalenes, chlorinated aromatics and chlorinated aliphatic hydrocarbons, such as chlorobenzenes, chloroethylenes or methylene chloride, aliphatic hydrocarbons, such as cyclohexane or paraffins, for example petroleum fractions, mineral and vegetable oils, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water.

As solid carriers there are suitable: for example ammonium salts and ground natural minerals, such as kaolins, clays, talc, chalk, quartz, attapulgite, montmorillonite or diatomaceous earth, and ground synthetic minerals, such as highly disperse silica, alumina and silicates, as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks; as emulsifying and/or foam-forming agents there are suitable: for example non-ionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates as well as albumin hydrolysis products; as dispersing agents rhere are suitable for example ligninsulphite waste liquors and methylcellulose.

Adhesives such as carboxymethylcellulose and natural and synthetic polymers in the form of powders, granules or latexes, such as gum arabic, polyvinyl alcohol and polyvinyl acetate, as well as natural phospholipids, such as cephalins and lecithins, and synthetic phospholipids, can be used in the formulations. Further additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 per cent by weight of active compound, preferably between 0.5 and 90%.

For combating weeds, the active compounds according to the invention, as such or in the form of their formulations, can also be used as mixtures with known herbicides, finished formulations or tank mixes being possible.

Possible components for the mixtures are known herbicides, such as, for example : aryloxalkanoic acids, such as 2,4 D, 2,4 DP, 2,4 DB, MCPA, MCPP, fluoroxypyr; aryloxy-phenoxyalkanoic esters, such as diclofop-methyl, fenoxaprop, fluoazifopbutyl, quizalofop, haloxyfop; arylcarboxylic acids, such as clopyralid; azinones, such as chloridazon, norflurazon; carbamates, such as phenmedipham; chloroacetanilides such as alachlor, metazachlor, metolachlor; dinitroanilines, such as oryzalin, pendimethalin, trifluoralin; diphenyl ethers, such as acifluorfen, bifenox, fomesafen, lactofen, oxyfluorfen; ureas, such as chlortoluron, fluormeturon, isoproturon, methabenzthiazuron; hydroxylamines, such as alloxydim, sethoxydim; imidazolinones, such as imazethapyr, imazamethabenz, imazaquin; nitriles, such as bromoxynil, ioxynil; oxyacetamides, such as mefenacet; sulphonylureas, such as bensulfuron, chlorimuron, chlorsulfuron, metsulfuron, thiameturon; thiocarbamates, such as cycloate, EPTC, molinate, tri-allate; triazines, such as atrazine, cyanazine, simazine, simetryne, terbutryne; triazinones, such as ethiozin, hexazinon, metamitron, metribuzin or bentazone, cinmethylin, fluridone, pyridate or dimethazone. Surprisingly, some mixtures also show a synergistic action.

Mixtures with other known active compounds, such as fungicides, insecticides, acaricides, nematicides, bird repellents, plant nutrients and agents which improve soil structure, are also possible.

The active compounds can be used as such, in the form of their formulations or in the use forms prepared therefrom by further dilution, such as ready-to-use solutions, suspensions, emulsions, powders, pastes and granules. They are used in the customary manner, for example by watering, spraying, atomizing or scattering.

The active compounds according to the invention can be applied either before or after emergence of the plants.

They can also be incorporated into the soil before sowing.

The amount of active compound used can vary within a substantial range. It depends essentially on the nature of the desired effect. In general, the amounts used are between 0.001 and 10 kg of active compound per hectare of soil surface, preferably between 0.005 and 5 kg per ha.

PREPARATION EXAMPLES

Example 1

2-[7-Fluoro-3H-1,4-benzoxazin-2(4H)-on-6-yl]-4,5,6,7-tetrahydro-2H-isoindole-1,3-dione

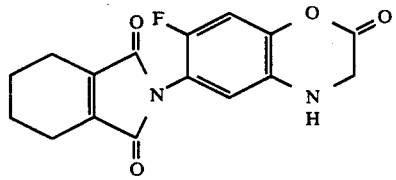

Process (a)

A mixture of 5 g (0.027 mol) 6-amino-7-fluoro-3H-1,4-benzoxazin-2(4H)-one, 4.2 g (0.027 mol) of 3,4,5,6-tetrahydrophthalic anhydride and 15 ml of glacial acetic acid is refluxed for 4 hours with stirring. The reaction mixture is introduced into ice-water, and the solid which has precipitated is filtered off with suction. After washing and drying, 6.5 g (76% of theory) of the abovementioned product are obtained, melting point: 228°–233° C.

Precursors

Example III-1

6Amino-7-fluoro-3H-1,4-benzoxazin-2(4H)-one

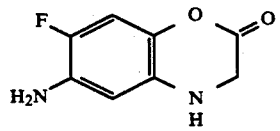

22 g (0.1 mol) of 6-nitro-7-fluoro-3H-1,4-benzoxaxin-2(4H)-one are introduced in portions at 60° C. into a suspension of 22 g (0.39 mol) of iron powder in 170 ml of 5 per cent acetic acid; during this process, the temperature of the suspension rises to 90° C. The mixture is stirred at 90° C. for another 30 minutes and, after cooling, the undissolved components are filtered off. The filtration residue is suspended repeatedly in warm methanol and the suspension is filtered. The combined methanol filtrates are concentrated, after which 13 g (71% of theory) of 6-amino-7-fluoro-3H-1,4-benzoxazin-2(4H)-one are obtained (m.p. >250° C.).

Example XVII-1

6-Nitro-7-fluoro 3H-1,4-benzoxazin-2(4H)-one

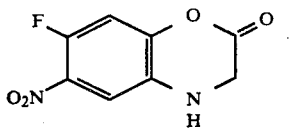

4.6 ml of 60 per cent strength nitric acid are added dropwise at −5° C. to 0° C. to a solution of 5 g (0.03 mol) of 7-fluoro-3H-1,4-benzoxazin-2(4H)-one in 50 ml of concentrated sulphuric acid. The mixture is then stirred for 1.5 hours at 0° C. and then transferred to ice and filtered off with suction, and residue is washed with water.

After drying, 4.8 g (75% of theory) of 6-nitro-7-fluoro-3H-1,4-benzoxazin-2(4H)-one with a melting point of 196°–202° C. are obtained.

Example XX-1

7-Fluoro-3H-1,4-benzoxazin-2(4H)-one

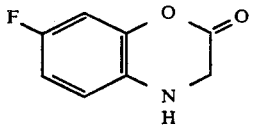

50 g (0.17 mol) of 5-fluoro-2-nitro-phenyl methylsulphonyloxyacetate are added in portions at 60° C. to a suspension of 5 g (0.89 mol) of iron powder in 450 ml of 5 per cent strength aqueous acetic acid. During this process, the temperature of the suspension rises to 90° C. The mixture is stirred for another 30 minutes at 90° C. and, after cooling, the undissolved components are filtered off. The filtration residue is suspended repeatedly in warm methanol and the suspension is filtered. After concentration, the combined methanol filtrates give 21.3 g (75% of theory) of 7-fluoro-3H-1,4-benzoxazin-2(4H)-one having a melting point of 199° C.

Example XIX-1

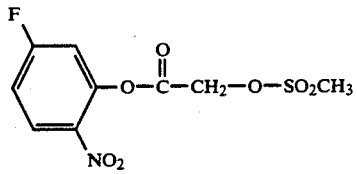

5-Fluoro-2-nitro-phenyl methylsulphonyloxyacetate

A solution of 92 g (0.53 mol) of methylsulphonyloxacetyl chloride in 250 ml of toluene is added dropwise over a period of 30 minutes to a solution of 92 g (0.40 mol) of 5-fluoro-2-nitrophenol and 81 ml (0.59 mol) of triethylamine in 250 ml of toluene The mixture is stirred overnight at room temperature, the triethylamine hydrochloride is filtered off, and the mixture is then evaporated to dryness.

This gives 80.4 g (69% of theory) of 5-fluoro-2-nitrophenyl methylsulphonyloxyacetate as a waxy solid, which can be reacted without further purification.

IR (CH2Cl2): 180, 1610, 1540 cm⁻¹.

Example 2

2-[7-Fluoro-4-propargyl-3H-1,4-benzoxazin-2(4H)-on-6-yl]-4,5,6,7-tetrah-ydro-2H-isoindole-1,3-dione

Process (1)

A solution of 3 g (0.0095 mol) of 2-[7-fluoro-3H-1,4-benzoxazin-2(4H)-on-6-yl]-4,5,6,7-tetrahydro-2H-isoindole-1,3-dione in 5 ml of tetrahydrofuran is added dropwise at 0° C. to a suspension of 0.42 g (0.014 mol, 80% in oil) of NaH in 5 ml of tetrahydrofuran. After the mixture has been stirred for 30 minutes at room temperature, 1.6 ml (0.014 mol, 80% in toluene) of propargyl bromide are added dropwise and the mixture is refluxed for 2 hours with stirring. Aqueous working-up gives 2.5 (74% of theory) of 2-[7-fluoro-4-propargyloxy-3H-1,4-benzoxazin-2(4H)-on-6-yl]-4,5,6,7-tetrahydro-2H-isoindole- 1-3, dione having a melting point of 189°–190° C.

Example 8

3-Chloro-2-[7-fluoro-4-proparggyl-3H-1,4-benzoxazin-2(4H)-on-6-yl]-4,5,6,7-tetrahydro-2H-indazole

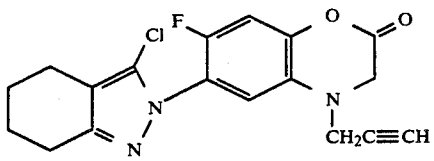

Process (f)

A mixture of 3 g (8.8 mmol) of 2-(7-fluoro-4-propargyl-3H-1,4-benzoxazin-2(4H)-on-6-yl)-2,3,4,5,6,7-hexahydro-2H-indazol-3-one and 2.5 ml (27 mmol) of phosphorus oxychloride is refluxed for 3 hours. After cooling, the residue is taken up in methylene chloride and washed successively with water, 5% sodium hydroxide solution and finally with water, after which it is dried and concentrated. After purifying the residue by column chromatography (silica gel, petroleum ether/ethyl acetate=2:1), 0.8 g (25% of theory) of 3-chloro-2-[7-fluoro-4-propargyl-3H-1,4-benzoxazin-2(4H)-on-6-yl]-4,5,6,7-tetrahydro-2H-indazole is obtained. Mass spectrum: m/z (% rel. int.) 359(80).

Precursors

Example IX-1

2-(7-Fluoro-4-propargyl-3H-1,4-benzoxazin-2(4H)-on-6-yl)-2,3,4,5,6,7-hexahydro-2H-indazol-3-one

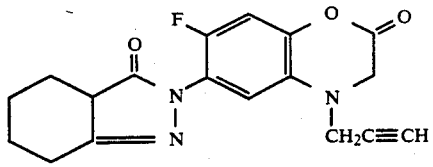

A mixture of 5 g (0.021 mol) of 7-fluoro-4-propargyl-3H-1,4-benzoxazin-2(4H)-on-6-ylhydrazine and 3.6 (0.021 mmol) of ethyl cyclohexane-2-carboxylate is refluxed for 6 hours in 70 ml of ethanol and 0.3 ml of concentrated hydrochloric acid. The mixture is cooled, poured into ice and the aqueous phase is extracted several times with methylene chloride. The combined organic phases are dried and concentrated by evaporation. 5.1 g (71% of theory) of 2-(7-fluoro-4-propargyl-3H-1,4-benzoxazin-2(4H)-on-6-yl)-2,3,4,5,6,7-hexahydro-2H-indazol-3-one are obtained in this manner..

Mass spectrum: m/z (% rel. int.): 341(110), 312(10), 246(15), 204(30).

Example VII-1

7-Fluoro-4-propargyl-3H-1,4-benzoxazin-2(4H)-on-6-ylhydrazine

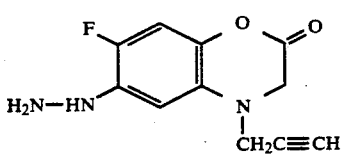

A saturated aqueous solution of 2,4 g (0.035 mol) of sodium nitrite is added dropwise to a solution of 6 g (0.027 mol) of 6-amino-7-fluoro-3H-1,4-benzoxazin-2-(4H)one in 30 ml of concentrated hydrochloric acid at 0° C. and the mixture is stirred for a further 2 hours at 0° C. The reaction mixtuer is cooled to −30° C. and a solution consisting of 13 g (0.069 mol) of tin(II0 chloride in 12 ml of concentrated hydrochloric acid is added dropwise. The mixture is stirred for a further 8 hours at 0° C., poured into ice and adjusted to a pH vlaue of 10 with 6 N sodium hydroxide solution. After filtering off with suction and drying the residue 6 g (94.5% of theory) of 7-fluoro-4-propargyl-3H-1,4-benzoxazin-2(4H)-on-6-ylhydrazine having a melting point of 146° C. are obtained.

The following nitrogen-containing N-aryl-heterocycles of the formula (I)

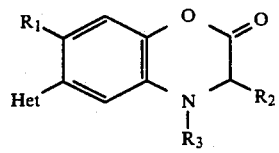

are obtained in a corresponding manner and following the general preparation instructions.

TABLE 1

| Example No. | R¹ | R² | R³ | Het | Melting point/°C. |
|---|---|---|---|---|---|
| 3 | F | H | —CH₂CN | 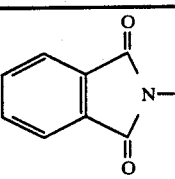 | 217–220 |
| 4 | F | H | —COCH₃ | " | 155–163 |
| 5 | F | H | —CO₂CH₂CH₂OCH₃ | " | 220 |
| 6 | F | H | —SO₂CH₃ | " | 203–208 |
| 7 | F | H | —CH₂—C≡CH | 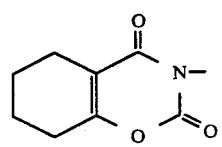 | 210.5–212 |

Example A

Post-emergence test

Solvent: 5 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

Test plants which have a height of 5–15 cm are sprayed with the preparation of the active compound in such a way as to apply the particular amounts of active compound desired per unit area. The concentration of the spray liquor is so chosen that the particular amounts of active compound desired are applied in 1000 l of water/ha. After three weeks, the degree of damage to the plants is rated in % damage in comparison with the development of the untreated control. The figures denote:

0% = no action (like untreated control)
100% = total destruction

In this test, a very good herbicidal action, combined with a good tolerance by crop plants is shown, for example, by the compounds of Example Nos.1,2,3,4,5 and 7.

Example B

Pre-emergence test

Solvent: 5 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

Seeds of the test plants are sown in normal soil and, after 24 hours, watered with the preparation of the active compound. It is expedient to keep constant the amount of water per unit area. The concentration of the active compound in the preparation is of no importance, only the amount of active compound applied per unit area being decisive. After three weeks, the degree of damage to the plants is rated in % damage in comparison with the development of the untreated control. The figures denote:

0%
100% = total destruction

In this test, a very good tolerance in monocotyledon and dicotyledon crops and a very good herbicidal action is shown, for example, by the compounds of Example Nos. 1,2,3,4 and 5.

It will be appreciated that the instant specification is set forth by way of illustration and not limitation, and that various modifications and changes may be made without departing from the spirit and scope of the present invention.

What is claimed is:

1. A nitrogen-containing N-aryl-heterocycle of the formula

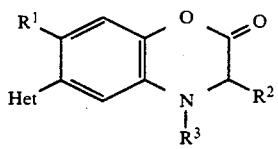

in which

Het represents a heterocycle of the formula

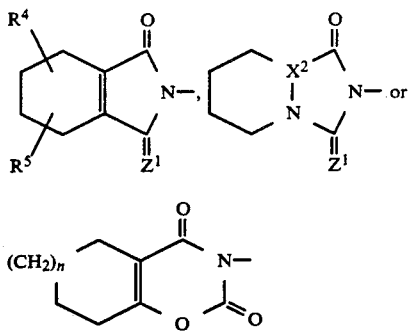

$R^1$ represents hydrogen or halogen,
$R^2$ represents hydrogen or alkyl,
$R^3$ represents hydrogen or in each case optionally substituted alkyl, alkenyl, alkynyl, cycloalkyl, cycloalkenyl, alkylsulphonyl, arylsulphonyl, alkylcarbonyl or alkoxycarbonyl,
$R^4$ and $R^5$ independently of one another in each case represent hydrogen or alkyl,
$R^6$ and $R^7$ either independently of one another in each case represent hydrogen or alkyl or together represent a divalent alkanediyl radical,
$R^8$ represents hydrogen, alkyl or optionally substituted aryl,
$R^9$ represents hydrogen, halogen, alkyl or halogenoalkyl,
$R^{10}$ represents hydrogen, alkyl or halogenoalkyl or $R^9$ and $R^{10}$ together represent a divalent alkanediyl,
$R^{11}$ represents hydrogen, halogen, alkyl or halogenoalkyl,
$R^{12}$ and $R^{13}$ independently of one another represent hydrogen, alkyl, alkoxyalkyl, halogenoalkyl, alkenyl, halogenoalkenyl, alkynyl or halogenoalkynyl, or represents optionally substituted cycloalkyl,
$R^{14}$ represents hydrogen, alkyl, halogenoalkyl, alkenyl, halogenoalkenyl, alkynyl or halogenoalkynyl or
$R^{13}$ and $R^{14}$ together represent divalent alkanediyl,
$X^1$ represents oxygen, a —CH$_2$— group or an

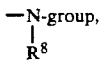

$X^2$ represents nitrogen or a CH group,
$Z^1$ represents oxygen or sulphur and
n represents the number 0 or 1.

2. A nitrogen-containing N-aryl-heterocycle according to claim 1, in which
$R^2$ represents hydrogen or alkyl having 1 to 4 carbon atoms,
$R^3$ represents hydrogen, alkyl having 1 to 8 carbon atoms, alkenyl having 2 to 8 carbon atoms, alkynyl having 3 to 8 carbon atoms, halogenoalkyl having 1 to 8 carbon atoms and 1 to 17 identical or different halogen atoms, halogenoalkenyl having 2 to 8 carbon atoms and 1 to 15 identical or different halogen atoms, halogenoalkynyl having 3 to 8 carbon atoms and 1 to 13 identical or different halogen atoms, alkylsulphonyl, cyanoalkyl, alkoxyalkyl, alkylthioalkyl, halogenoalkoxyalkyl, alkoxyalkoxyalkyl, bis-(alkoxy)alkyl, bis-(alkylthio)alkyl, alkylcarbonyl, alkoxycarbonyl, alkylcarbonylalkyl, alkoxycarbonylalkyl or alkoxyalkoxycarbonylalkyl, each of which has 1 to 8 carbon atoms in the individual alkyl moieties and where appropriate 1 to 9 identical or different halogen atoms, or represents cycloalkyl, ccyloalkenyl, cycloalkyloxycarbonylalkyl or cycloalkylalkyl, each of which has 3 to 7 carbon atoms in the cycloalkyl moiety and where appropriate 1 to 4 carbon atoms in the alkyl moiety and each of which is optionally monosubstituted or polysubstituted by identical or different substituents, the substituents in the cycloalkyl mciety in each case being selected from the group consisting of halogen, and alkyl or alkoxy in each case having 1 to 4 carbon atoms, or $R^3$ represents oxetanylalkyl, tetrahydrofuranylalkyl or tetrahydropyranylalkyl, each of which has 1 to 3 carbon atoms in the alkyl moieties and each of which is optionally substituted by alkyl having 1 to 4 carbon atoms, or represents aralkyl which has 6 to 10 carbon atoms in the aryl moiety and 1 to 4 carbon atoms in the alkyl moiety, or arylsulphonyl which has 6 to 10 carbon atoms, the aralkyl or arylsulphonyl substituents being optionally substituted on the aryl moiety by at least one member selected from the group consisting of halogen, cyano, nitro, and alkyl, alkoxy, alkylthio or alkoxycarbonyl each of which has 1 to 4 carbon atoms, and halogenoalkyl, halogenoalkoxy or halogenoalkylthio each of which has 1 to 4 carbon atoms and 1 to 9 identical or different halogen atoms, $R^4$ and $R^5$ independently of one another in each case represent hydrogen or alkyl having 1 to 4 carbon atoms, $R^6$ and $R^7$ either independently of one another in each case represent hydrogen or alkyl having 1 to 4 carbon atoms, or together represent a divalent alkanediyl radical having 2 to 7 carbon atoms, $R^8$ represents hydrogen, or alkyl having 1 to 4 carbon atoms, or represents phenyl which is optionally substituted by identical or different substituents selected from the group consisting of halogen, cyano, nitro, and alkyl, alkoxy or alkylthio each of which has 1 to 4 carbon atoms, and halogenoalkyl, halogenoalkoxy or halogenoalkylthio each of which has 1 to 4 carbon atoms and 1 to 9 identical or different halogen atoms, $R^9$ represents hydrogen, fluorine, chlorine, bromine, iodine, alkyl having 1 to 6 carbon atoms, or halogenoalkyl having 1 to 4 carbon atoms and 1 to 9 identical or different halogen atoms, and $R^{10}$ represents hydrogen, alkyl having 1 to 6 carbon atoms, or halogenoalkyl having 1 to 4 carbon atoms and 1 to 9 identical or different halogen atoms, or $R^9$ and $R^{10}$ together represent a divalent alkanediyl radical having 2 to 6 carbon atoms, $R^{11}$ represents hydrogen, fluorine, chlorine, bromine, iodine, alkyl having 1 to 6 carbon atoms, or halogenoalkyl having 1 to 4 carbon atoms and 1 to 9 identical or different halogen atoms, $R^{12}$ represents hydrogen, alkyl having 1 to 6 carbon atoms, alkenyl having 3 to 6 carbon atoms, alkynyl having 3 to 6 carbon atoms, halogenoalkyl having 1 to 4 carbon atoms and 1 to 9 identical or different halogen atoms, halogenoalkenyl having 3 to 6 carbon atoms and 1 to 5 identical or different halogen atoms, halogenoalkynyl having 3 to 6 carbon atoms and 1 to 5 identical or different halogen atoms, or alkoxyalkyl having 1 to 4 carbon atoms in each of the individual alkyl moieties, or represents cycloalkyl which has 3 to 7 carbon atoms and which is optionally substituted by identical or different substituents selected from the group consisting of halogen and alkyl or alkoxy each of which has 1 to 4 carbon atoms, $R^{13}$ represents hydrogen, alkyl having 1 to 6 carbon atoms, alkenyl having 3 to 6 carbon atoms, alkynyl having 3 to 6 carbon atoms, halogenoalkyl having 1 to 4 carbon atoms and 1 to 9 identical or different halogen atoms, halogenoalkenyl having 3 to 6 carbon atoms and 1 to 5 identical or different halogen atoms, halogenoalkynyl having 3 to 6 carbon atoms and 1 to 5 identical or different halogen atoms, or alkoxyalkyl having 1 to 4 carbon atoms in each of the individual alkyl moieties, or represents cycloalkyl which has 3 to 7 carbon atoms and which is optionally substituted by identical or different substituents selected from the group consisting of halogen and alkyl or alkoxy, each of which has 1 to 4 carbon atoms, and $R^{14}$ represents hydrogen, alkyl having 1 to 6 carbon atoms, alkenyl having 3 to 6 carbon atoms, alkynyl having 3 to 6 carbon atoms, halogenoalkyl having 1 to 4 carbon atoms and 1 to 9 identical or different halogen atoms, halogenoalkenyl having 3 to 6 carbon atoms and 1 to 5 identical or different halogen atoms, or halogenoalkynyl having 3 to 6 carbon atoms and 1 to 5 identical or different halogen atoms, or $R^{13}$ and $R^{14}$ together represent a divalent alkanediyl radical having 2 to 6 carbon atoms, $X^1$ represents oxygen, a $CH_2$ group or a

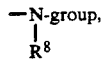
—N-group,
    |
    $R^8$ $X^2$ represents nitrogen or a CH group,
$Z^1$ represents oxygen or sulphur and
n represents the number 0 or 1.

3. A nitrogen-containing N-aryl-heterocycle according to claim 1, in which
Het represents a heterocyclo of the formula

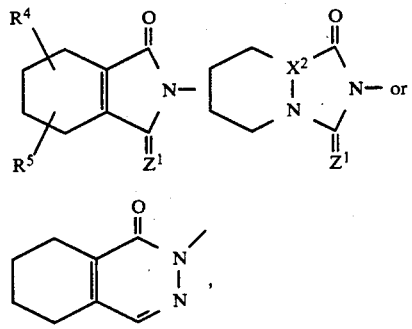

$R^1$ represents hydrogen, fluorine, chlorine or bromine,
$R^2$ represents hydrogen, methyl or ethyl,
$R^3$ represents methyl, ethyl, n- or i-propyl, n-, i-, s- or t-butyl, or represents allyl or propargyl, or represents in each case straight-chain or branched pentyl, hexyl, butenyl, pentenyl, hexenyl, butynyl, pentynyl, or hexynyl, and furthermore represents halogenoalkyl having 1 to 4 carbon atoms or halogenoalkenyl having 3 to 5 carbon atoms and in each case 1 to 8 identical or different halogen atoms, or represents cycloalkyl, alkoxyalkyl, alkylthioalkyl, halogenoalkoxyalkyl, alkoxyalkoxyalkyl, alkylsulphonyl, alkylcarbonyl, alkoxycarbonyl, alkylcarbonylalkyl, alkoxycarbonylalkyl or alkoxyalkoxycarbonylalkyl, each of which has 1 to 5 carbon atoms in the individual alkyl moieties, or furthermore represents cyclopropylmethyl, cyclopentylmethyl, cyclohexylmethyl, cyclopropyloxycarbonylmethyl, cyclopentyloxycarbonylmethyl, cyclohexyloxycarbonylmethyl, cyclopropyl, cyclopentyl or cyclohexyl, each of which is optionally monosubstituted to trisubstituted by identical or different substituents from the group consisting of methyl, methoxy, fluorine and chlorine, or represents oxetanylmethyl, oxetanylethyl, tetrahydrofuranylmethyl, tetrahydrofuranylethyl, tetrahydropyranylmethyl or tetrahydropyranylethyl, each of which is optionally substituted by at least one of methyl and ethyl, or represents benzyl or phenylethyl, each of which is optionally monosubstituted to trisubstituted by identical or different substituents, selected from the group consisting of fluorine, chlorine, bromine, cyano, nitro, methyl, ethyl, n- or i-propyl, n-, i-, s- or t-butyl, methoxy, ethoxy, n- or i-propoxy, methylthio, ethylthio, methoxycarbonyl, ethoxycarbonyl, trifluoromethyl, trifluoromethoxy and trifluoromethylthio, $R^4$ and $R^5$ independently of one another in each case represent hydrogen, methyl, ethyl or n- or i-propyl, $R^6$ and $R^7$ independently of one another in each case represent hydrogen, methyl, ethyl or n- or i-propyl or together represent a divalent alkanediyl radical having 2 to 5 carbon at.oms, $R^8$ represents hydrogen, methyl, ethyl or n- or i-propyl, or represents phenyl which is optionally monosubstituted to trisubstituted by identical or different substituents selected from the group consisting of fluorine, chlorine, bromine, cyano, nitro, methyl, ethyl, n- or i-propyl, n-, i-, s- or t-butyl, methoxy, ethoxy, n- or i-propoxy, methylthio, trifluoromethyl, trifluoromethoxy and trifluoromethylthio, $R^9$ represents hydrogen, fluorine, chlorine, bromine, methyl, ethyl, n- or i-propyl, n-, i-, s- or t-butyl, fluoromethyl, difluoromethyl, trifluoromethyl, chloromethyl, dichloromethyl, trichloromethyl, difluorochloromethyl or dichlorofluoromethyl, and $R^{10}$ represents hydrogen, methyl, ethyl, n- or i-propyl, n-, i-, s- or t-butyl, fluoromethyl, difluoromethyl, trifluoromethyl, chloromethyl, dichloromethyl, trichloromethyl, difluorochloromethyl or dichlorofluoromethyl, or $R^9$ and $R^{10}$ together represent a 1,3-propanediyl radical, a 1,4-butanediyl radical or a 1,5-pentanediyl radical, $R^{11}$ represents hydrogen, fluorine, chlorine, bromine, methyl, ethyl, n- or i-propyl, n-, i-, s- or t-butyl, fluoromethyl, difluoromethyl, trifluoromethyl, chloromethyl, dichloromethyl, trichloromethyl, difluorochloromethyl or dichlorofluoromethyl, $R^{12}$ represents hydrogen, methyl, ethyl, n- or i-propyl or n-, i-, s- or t-butyl, or methyl, ethyl or t-butyl, each of which is monosubstituted, disubstituted or trisubstituted by at least one of fluorine and chlorine, or represents allyl, n- or i-butenyl, chloroallyl, dichloroallyl, propargyl, chloropropargyl or methoxymethyl, or represents cyclopropyl, cyclopentyl or cyclohexyl, each of which is optionally monosubstituted to pentasubstituted by identical or different substituents from the group consisting of fluorine, chlorine, methyl and methoxy, $X^1$ represents oxygen, a $CH_2$ group or an

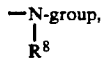

$X^2$ represents nitrogen or a CH group, and $Z^1$ represents oxygen or sulphur.

4. A nitrogen-containing N-aryl-heterocycle according to claim 1, in which

Het represents

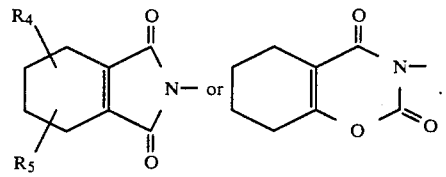

5. A compound according to claim 1, wherein such compound is 2-[7-fluoro-3H-1,4-benzoxazin-2(4H)-on-6-yl]-4,5,6,7-tetrahydro-2H-isoindole-1,3-dione of the formula

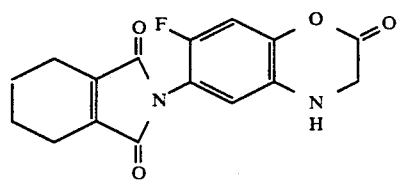

6. A compound according to claim 1, wherein such compound is 2-[7-fluoro-4-propargyl-3H-1,4-benzoxazin-2(4H)-on-6-yl]-4,5,6,7-tetrahydro-2H-isoindole-1,3-dione of the formula

7. A compound according to claim 1, wherein such compound is 2-[7-fluoro-4-propargyl-3H-1,4-benzoxazin-2(4H)-on-6-yl]-5,6,7,8-tetrahydro-benzo-1,3-oxazine-2,4-dione of the formula

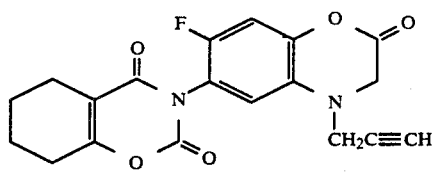

8. A herbicidal composition comprising a herbicidally effective amount of a compound according to claim 1 and a diluent.

9. A method of combating unwanted vegetation which comprises applying to such vegetation or to a locus in which such vegetation is growing or is to be grown a herbicidally effective amount of a compound according to claim 1.

10. The method according to claim 9, wherein such compound is

2-[7-fluoro-3H-1,4-benzoxazin-2(4H)-on-6-yl]-4,5,6,7-tetrahydro-2H-isoindole-1,3-dione, 2-[7-fluoro-4-propargyl-3H-1,4-benzoxazin-2(4H)-on-6-yl]-4,5,6,7-tetrahydro-2H-isoindole-1,3-dione, 2-[7-fluoro-4-propargyl-3H-1,4-benzoxazin-2(4H)-on 6-yl]-5,6,7,8-tetrahydro-benzo-1,3-oxazine-2,4-dione.

11. A compound of the formula

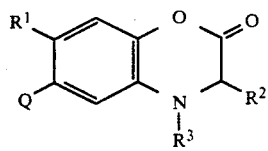

in which

R¹ represents hydrogen or halogen,

R² represents hydrogen or alkyl,

R³ represents hydrogen or in each case optionally substituted alkyl, alkenyl, alkinyl, cycloalkyl, cycloalkenyl, alkylsulphonyl, arylsulphonyl, alkylcarbonyl or alkoxycarbonyl, Q represents $NH_2$ or $-NH-NH_2$, or

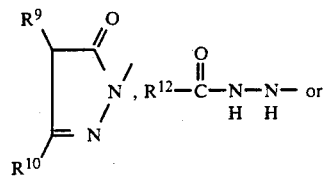

$R^9$ represents hydrogen, halogen, alkyl or halogenalkyl, $R^{10}$ represents hydrogen, alkyl or halogenalkyl, $R^{12}$ represents hydrogen, alkyl, alkoxyalkyl, halogenalkyl, alkenyl, halogenoalkyl, alkinyl, halogenalkynyl or optionally substituted cycloalkyl, $R^{13-1}$ and $R^{14-2}$ together represent a divalent alkanediyl radical.

* * * * *